United States Patent
Dupau et al.

(10) Patent No.: US 9,090,534 B2
(45) Date of Patent: Jul. 28, 2015

(54) SELECTIVE HYDROGENATION OF ALDEHYDE WITH RU/BIDENTATE LIGANDS COMPLEXES

(71) Applicant: FIRMENICH SA, Geneva (CH)

(72) Inventors: Philippe Dupau, Geneva (CH); Lucia Bonomo, Geneva (CH); Laurent Kermorvan, Geneva (CH)

(73) Assignee: Firemenich SA, Geneva (CH)

( * ) Notice: Subject to any disclaimer, the term of this patent is extended or adjusted under 35 U.S.C. 154(b) by 0 days.

(21) Appl. No.: 14/349,811

(22) PCT Filed: Sep. 27, 2012

(86) PCT No.: PCT/EP2012/069123
§ 371 (c)(1),
(2) Date: Apr. 4, 2014

(87) PCT Pub. No.: WO2013/050297
PCT Pub. Date: Apr. 11, 2013

(65) Prior Publication Data
US 2014/0243526 A1     Aug. 28, 2014

(30) Foreign Application Priority Data
Oct. 6, 2011   (EP) .................................... 11184149

(51) Int. Cl.
| | | |
|---|---|---|
| *C07F 15/00* | (2006.01) | |
| *C07C 29/14* | (2006.01) | |
| *C07C 29/141* | (2006.01) | |
| *B01J 31/18* | (2006.01) | |
| *B01J 31/22* | (2006.01) | |
| *B01J 31/24* | (2006.01) | |
| *C07B 41/02* | (2006.01) | |
| *C07C 29/145* | (2006.01) | |
| *C07C 45/64* | (2006.01) | |

(52) U.S. Cl.
CPC ............. *C07C 29/141* (2013.01); *B01J 31/181* (2013.01); *B01J 31/1805* (2013.01); *B01J 31/2226* (2013.01); *B01J 31/24* (2013.01); *B01J 31/2409* (2013.01); *C07B 41/02* (2013.01); *C07C 29/145* (2013.01); *C07C 45/64* (2013.01); *B01J 2231/643* (2013.01); *B01J 2531/0238* (2013.01); *B01J 2531/821* (2013.01); *C07B 2200/07* (2013.01); *C07C 2101/02* (2013.01); *C07C 2101/04* (2013.01); *C07C 2101/10* (2013.01); *C07C 2101/16* (2013.01); *C07C 2101/18* (2013.01); *C07C 2102/42* (2013.01)

(58) Field of Classification Search
CPC ..... C07F 15/0033; B01J 31/24; B01J 31/181; B01J 31/1805; B01J 31/2226; B01J 31/2409; C01B 41/02
USPC .................. 556/18, 21, 36; 544/225; 546/12; 549/212; 568/838, 881
See application file for complete search history.

(56) References Cited

U.S. PATENT DOCUMENTS

| | | | |
|---|---|---|---|
| 4,321,414 A | 3/1982 | Costa | |
| 6,720,439 B1 | 4/2004 | Ohkuma et al. | |

FOREIGN PATENT DOCUMENTS

| | | |
|---|---|---|
| EP | 0 901 997 A1 | 3/1999 |
| EP | 1 741 693 A1 | 1/2007 |
| EP | 1 813 621 A1 | 8/2007 |
| WO | WO 01/74829 A1 | 10/2001 |
| WO | WO 02/22526 A2 | 3/2002 |
| WO | WO 02/40155 A1 | 5/2002 |
| WO | WO 2008/065588 A1 | 6/2008 |
| WO | WO 2009/055912 A1 | 5/2009 |
| WO | WO 2010/038209 A1 | 4/2010 |
| WO | WO 2010/038209 A8 | 4/2010 |
| WO | WO 2011/145032 A2 | 11/2011 |

OTHER PUBLICATIONS

International Search Report and Written Opinion, application No. PCT/EP2012/069123, mailed Dec. 6, 2012.

*Primary Examiner* — Porfirio Nazario Gonzalez
(74) *Attorney, Agent, or Firm* — Winston & Strawn LLP

(57) ABSTRACT

The present invention relates to processes for the reduction by hydrogenation, using molecular $H_2$, of a $C_5$-$C_{20}$ substrate containing one or two aldehydes functional groups into the corresponding alcohol or diol, characterized in that said process is carried out in the presence of —at least one catalyst or pre-catalyst in the form of a ruthenium complex having a coordination sphere of the $N_2P_2O_2$, wherein the coordinating atoms $N_2$ are provided by a first bidentate ligand, the coordinating atoms $P_2$ are provided by a second bidentate ligand and the coordinating atoms $O_2$ are provided by two non-linear carboxylate ligands; and—optionally of an acidic additive.

9 Claims, 2 Drawing Sheets

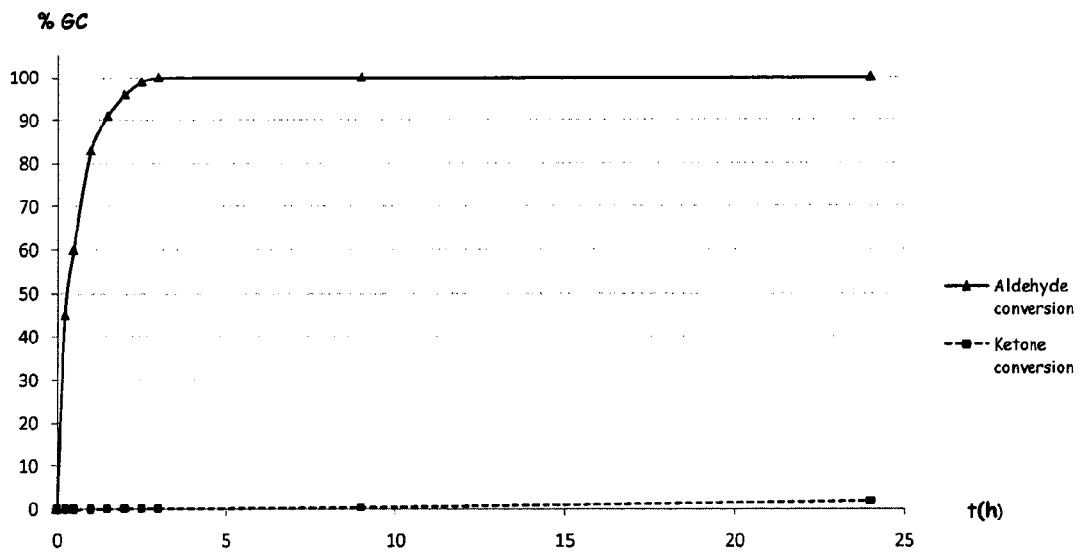
Figure 1a: Graph showing the selectivity of 2-methyl-4-((R)-2,2,3-trimethylcyclopent-3-en-1-yl)pent-4-enal versus (R,E)-3,3-dimethyl-5-(2,2,3-trimethyl-cyclopent-3-en-1-yl)pent-4-en-2-one
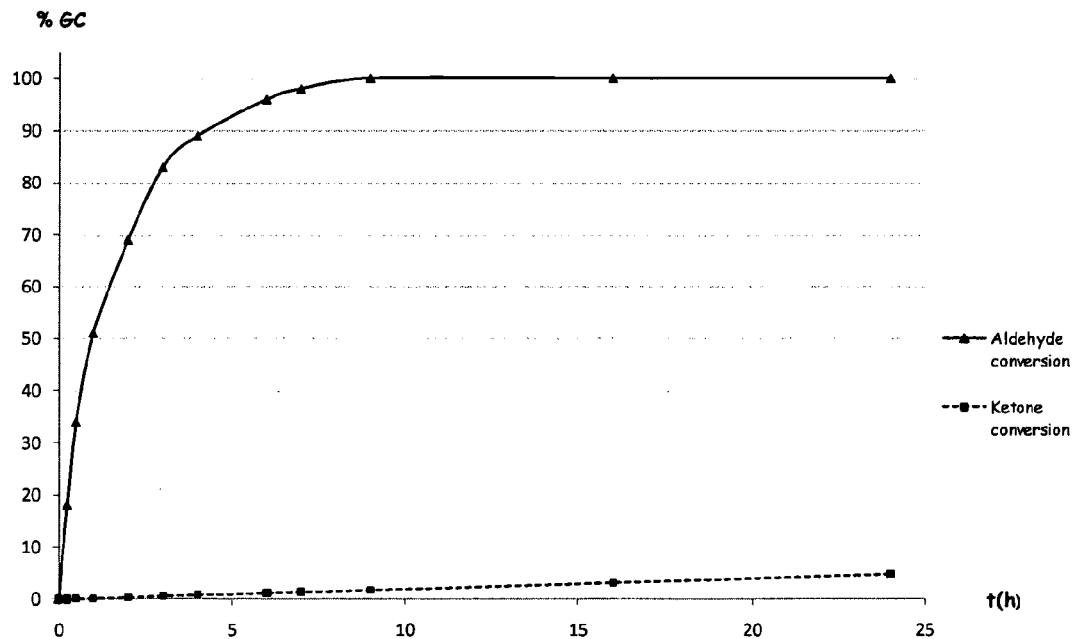
Figure 1b: Graph showing the selectivity of 2-methyl-4-((R)-2,2,3-trimethylcyclopent-3-en-1-yl)pent-4-enal versus trans 1-(2,2,6-trimethylcyclohexyl)hexan-3-one

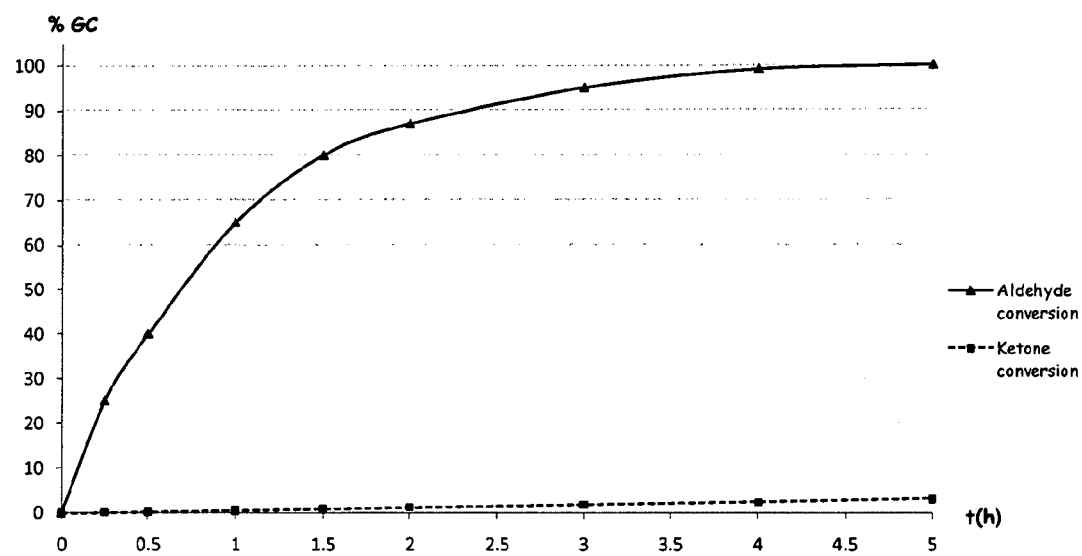
Figure 2: Graph showing the selectivity of 2-methyl-4-((R)-2,2,3-trimethylcyclopent-3-en-1-yl)pent-4-enal versus acetophenone

SELECTIVE HYDROGENATION OF ALDEHYDE WITH RU/BIDENTATE LIGANDS COMPLEXES

This application is a 371 filing of International Patent Application PCT/EP2012/069123 filed Sep. 27, 2012, which claims the benefit of European patent application no. 11184149.0 filed Oct. 6, 2011.

TECHNICAL FIELD

The present invention relates to the field of catalytic hydrogenation and to the use of ruthenium complexes having a coordination sphere of the $N_2P_2O_2$, wherein the coordinating atoms $O_2$ are provided by two carboxylate ligands, in hydrogenation processes for the reduction of aldehydes into the corresponding alcohol.

PRIOR ART

Reduction of an aldehyde into the corresponding alcohol is one of the fundamental reactions in organic chemistry, and is used in a large number of chemical processes. The most convenient manner to achieve such reduction is to use a hydrogenation (using $H_2$) process.

Several types of catalysts performing hydrogenation of carbonyl groups has been described in the last years and the most relevant ones are Ru complexes having a $P_2N_2$ coordination sphere, and more precisely a $P_2N_2Cl_2$ coordination sphere, which reduces indistinctly an aldehyde or a ketone and do require the presence of a base in the medium (e.g. see EP 0901997, EP 1813621, WO09/055912, WO02/022526 or WO02/40155). However as mentioned said systems all requires the presence of a strong base and this limitation hampers such catalytic systems to be industrially used with base sensitive substrate like most of aldehydes.

Only few catalytic systems for the aimed reduction have been reported to be active in the absence of a base (and generally displaying low reactivity) and none in the presence of a weak acid. For instance EP 1741693 or U.S. Pat. No. 6,720,439 recites the use of Ru complexes having a $P_2N_2HY$ coordination sphere (Y being an anion like Cl), however such system is described as being active only for the reduction of ketones. Alternatively, WO02/022526 mentions that [Ru(PN)$_2$(CH$_3$(CH$_2$)$_{0-1}$COO)$_2$] can be effective for the base-free reduction of base insensitive aromatic ketones.

The patent application WO2001/74829 reports the use of a cyclophane-diphosphine ruthenium complex of formula [(cyclophane-diphosphine)(diamines)RuX$_2$], wherein X is halide or carboxylate. However such document does mention only CF$_3$COO as a carboxylate anionic ligand, i.e. a carboxylate of different nature compared to the one of the invention, and report the use of those complexes only in the reduction of ketones, while in the present invention the catalysts are displaying efficient reactivity only in the reduction of aldehydes.

The patent application WO2010/038209 reports the use of bidentate phosphi-phosphine oxide ruthenium complex of formula [(phosphi-phosphine oxide) (diamines)RuX$_2$], but this complex requires in general a base and is not selective toward ketones.

Therefore, aldehydes being generally sensitive to basic conditions, there is still a need for efficient hydrogenation processes allowing the base-free selective reduction of aldehyde in the presence of olefins, and also displaying selectivity towards ketones.

To the best of our knowledge, the prior art does not report or suggest that the presently claimed catalysts (having branched carboxylates as coordinated anions) are indeed active in the free-base reduction of aldehydes and that are selective toward ketones and other functional groups such as olefins for example.

DESCRIPTION OF THE INVENTION

In order to overcome the problems aforementioned, the present invention relates to processes for the reduction by hydrogenation, using molecular $H_2$, of a $C_5$-$C_{20}$ substrate containing one or two aldehydes functional groups into the corresponding alcohol or diol, characterized in that said process is carried out in the presence of at least one catalyst or pre-catalyst in the form of a ruthenium complex having a coordination sphere of the $N_2P_2O_2$, wherein the coordinating atoms $N_2$ are provided by a first bidentate ligand, the coordinating atoms $P_2$ are provided by a second bidentate ligand and the coordinating atoms $O_2$ are provided by two non-linear carboxylate ligands; and optionally of an acidic additive.

As well understood by a person skilled in the art, by "bidentate" it is understood that said ligand coordinates the Ru metal with two atoms (e.g. two N or two P).

According to a particular embodiment of the invention, the substrate can be a compound of formula (I)

wherein $R^a$ represents a $C_4$-$C_{19}$ linear, branched or cyclic alkyl, alkenyl or alkadienyl group optionally comprising an aromatic ring and optionally comprising one, two or three functional groups selected among ketone, ether, carbon-carbon double or triple bond and carboxylic groups.

It is important to point out that the substrate may contain also functional groups such as ketones, indeed one of the advantages of said process is that the hydrogenation is particularly selective and it is possible to selectively hydrogenate the aldehyde group to without reducing a ketone group which may be present in the starting substrate.

The corresponding alcohols (I-a) of said substrate (I), are of formula

wherein $R^a$ is defined as in formula (I).

It is understood that by "a linear, branched or cyclic alkyl, alkenyl or alkadienyl group" it is meant that said $R^a$ can be in the form of, e.g., a linear alkyl group or can also be in the form of a mixture of said type of groups, e.g. a specific $R^a$ may comprise a branched alkenyl, a (poly)cyclic alkyl and a linear alkyl moiety, unless a specific limitation to only one type is mentioned. Similarly, in all the below embodiments of the invention, when a group is mentioned as being an alkenyl or alkadienyl, it is meant that said group comprises one or two carbon-carbon double bonds which can be conjugated or not with the aldehyde group or between them, in the case of alkadienyl. Similarly, in all the below embodiments of the invention, when a group is mentioned as being in the form of more than one type of topology (e.g. linear, cyclic or branched) and/or unsaturation (e.g. alkyl or alkenyl) it is meant also a group which may comprise moieties having any one of said topologies or unsaturations, as explained above. Similarly, in all the below embodiments of the invention, when a group is mentioned as being in the form of one type of unsaturation, (e.g. alkyl), it is meant that said group can be in any type of topology (e.g. linear, cyclic or branched) or having several moieties with various topologies.

According to any one of the invention's embodiments, the substrate is an aldehyde that will provide an alcohol that is useful in the pharmaceutical, agrochemical or perfumery industry as final product or as an intermediate. Particularly preferred substrate is an aldehyde that will provide an alcohol which is useful in the perfumery industry as final product or as an intermediate.

According to any one of the invention's embodiments, the substrate is a $C_5$-$C_{20}$ compound of formula (I), and in particular one may cite those wherein $R^a$ represents:

a $C_4$-$C_{19}$ group of formula

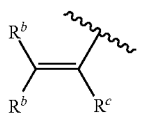

(a)

wherein $R^c$ represents a hydrogen atom or a $C_{1-3}$ alkyl group and each $R^b$, independently from each other, represents a hydrogen atom, a linear, branched or cyclic alkyl or alkenyl group optionally comprising an aromatic ring and optionally comprising one or two functional groups selected among ketone, ether, carbon-carbon triple bond and carboxylic groups; two of said $R^b$ and $R^c$ groups may be bonded together to form a $C_{5-7}$ ring optionally comprising one or two functional groups selected among ketone and ether groups, provided that at least one $R^b$ group is not a hydrogen atom;

a $C_4$-$C_{19}$ linear, branched or cyclic deconjugated alkenyl or alkadienyl group optionally comprising an aromatic ring and optionally comprising one or two functional groups selected among ketone, ether, carbon-carbon triple bond and carboxylic groups;

a $C_4$-$C_{19}$ linear, branched or cyclic alkyl group optionally comprising an aromatic ring and optionally comprising one or two functional groups selected among ketone, ether, carbon-carbon triple bond and carboxylic groups.

According to any one of the invention's embodiments, the substrate is a $C_5$-$C_{16}$ compound of formula (I) wherein $R^a$ represents:

a $C_4$-$C_{15}$ group of formula

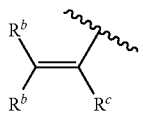

(a)

wherein $R^c$ represents a hydrogen atom or a $C_{1-3}$ alkyl group and each $R^b$, independently from each other, represents a linear, branched or cyclic alkyl or alkenyl group optionally comprising one functional group selected among ketone, ether and carboxylic groups;

a $C_4$-$C_{15}$ linear, branched or cyclic deconjugated alkenyl or alkadienyl group optionally comprising an aromatic ring and optionally comprising one functional group selected among ketone, ether and carboxylic groups;

a $C_4$-$C_{15}$ linear, branched or cyclic alkyl group optionally comprising an aromatic ring and optionally comprising one functional group selected among ketone, ether and carboxylic groups.

It is understood that by "deconjugated alkenyl or alkadienyl group" it is meant that the carbon-carbon double bonds are not conjugated with the aldehyde functional group.

Non-limiting examples of substrates of formula (I) are the following:

$C_{5-16}$ aldehydes such as:
2,3-dimethylbut-2-enal, cyclohex-3-enecarbaldehyde, 3-methylhex-2-enal, 6-oxoheptanal, (Z)-oct-5-enal, 3,7-trimethyl-octa-2,6-dienal, 3,7-dimethyloct-6-enal, (2,2-dimethyl-3-(2-oxopropyl)cyclopropyl)acetaldehyde, (3-acetyl-2,2-dimethylcyclobutyl)acetaldehyde, 3,6,7-trimethyl-octa-2,6-dienal, 3,6,7-trimethyloct-6-enal, undec-10-enal, endo 2-(3-(2-oxopropyl)bicyclo[2.2.1]heptan-2-yl)acetaldehyde, (E)-4-methyl-5-(p-tolyl)pent-4-enal, 2,2-dimethyl-6-methylene-7-(3-oxobutyl)cycloheptane carbaldehyde, 4-(3,3-dimethyl-2-(3-oxobutyl)cyclobutyl) pent-4-enal;
said compounds are all known to be highly base-sensitive substrates even at room temperature.

In the present invention, contrary to almost all the examples in the prior art, the presence of a base is avoided. This is an advantage, since it allows significant increases in yields for the production of alcohols from base-sensitive aldehydes. Therefore, according to anyone of the invention's embodiments, the substrate is a base-sensitive compound.

According to any one of the invention's embodiments, the ruthenium complex can be of the general formula

[Ru(PP)(NN)(RCOO)$_2$]  (1)

wherein PP represents a $C_6$-$C_{50}$ bidentate ligand wherein the coordinating groups are two phosphino groups;
NN represents a $C_2$-$C_{20}$ bidentate ligand wherein the coordinating groups are two amino groups; and
each R represents, simultaneously or independently, a $C_2$-$C_{12}$ hydrocarbon group branched or cyclic in the α and/or β position, and said hydrocarbon group is optionally comprising one to five heteroatoms selected amongst halogen, oxygen and nitrogen atoms.

According to any one of the invention's embodiments, in formula (1), each R represents, simultaneously or independently:
a $C_{2-12}$ alkyl group branched or cyclic in the α and/or β position
optionally substituted by one phenyl group optionally substituted by one to five halogen atoms and/or by $C_{1-4}$ alkyl or alkoxyl groups; and
optionally comprising one OH, amino or ether functional group;
or
a phenyl group optionally substituted by one to three, or five, halogen atoms and/or by $C_{1-4}$ alkyl or alkoxyl groups and/or by nitro groups.

According to a particular embodiment of the formula (1), said R group represents
a branched $C_{3-10}$ alkyl group comprising in the α position a tertiary or quaternary carbon atom and/or in the β position a quaternary carbon atom and also optionally comprising one OH, one ether functional group or one phenyl group, the phenyl group being optionally substituted by one or two halogen atoms and/or by $C_{1-4}$ alkyl or alkoxyl groups;

a $C_2$ alkyl group comprising in the α position one OH or one ether functional group; or a phenyl group optionally substituted by one, two or three halogen atoms and/or by $C_{1-4}$ alkyl or alkoxyl groups and/or nitro groups.

According to a particular embodiment of the formula (1), said R group represents a branched $C_{3-10}$ alkyl group comprising in the α position a tertiary or quaternary carbon atom and/or in the β position a quaternary carbon atom; or a phenyl group optionally substituted by one, two or three halogen atoms and/or by $C_{1-4}$ alkyl or alkoxyl groups and/or nitro groups.

For the sake of clarity, by the expression "α position" it is meant the usual meaning in the art, i.e. the carbon atom directly bound to the COO moiety of the group RCOO Similarly by the expression "β position" it is meant a carbon atom directly bound to the α position. For the sake of clarity, by the expression "group branched or cyclic" it is meant a group which is not linear, i.e. a cyclohexyl, a iso-propyl, or $ClCH_2$ but not $CH_2CH_3$ or $CCl_3$, and it is also clear that the branching may be due to one or several carbon atoms or an optional functional group, which may be part of a cycle or not.

As non-limiting examples of suitable RCOO group of (I), one may cite the isobutyrate, pivalate, $^tBu$-acetate, 2-Et-hexanoate, cyclohexanecarboxylate, picolinate, to cinnamate, benzoate, 4-Me-benzoate, 4-OMe-benzoate, 3,5-dichloro-benzoate, 2,4-dichloro-benzoate, isovalerate, adamantate or sec-butyrate.

According to any one of the invention's embodiments, the bidentate NN ligand is a compound of formula

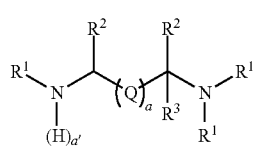

(B)

wherein a and a', simultaneously or independently, represent 0 or 1 (when a' is 0 then the nitrogen atom is part of an aromatic heterocycle);

the $R^1$, taken separately, represent, simultaneously or independently, a hydrogen atom or a $C_{1-6}$ linear, branched or cyclic alkyl group or a benzyl group optionally substituted; two $R^1$, taken together, may form a saturated heterocycle containing 5 to 7 atoms and including the atoms to which said $R^1$ are bonded, said heterocycle being optionally substituted;

$R^2$ and $R^3$, taken separately, represent, simultaneously or independently, a hydrogen atom, a $C_{1-6}$ linear, branched alkyl group or a $C_{6-10}$ aromatic group optionally substituted; a $R^1$ and an adjacent $R^2$, taken together, may form a saturated or aromatic heterocycle containing 5 to 8 atoms and including the atoms to which said $R^1$ and $R^2$ are bonded, and optionally containing one additional nitrogen or oxygen atom; two $R^2$, taken together, may form a saturated or unsaturated ring having 5 to 8 atoms and including the carbon atoms to which said $R^2$ or $R^3$ groups are bonded, said ring optionally containing one additional nitrogen and/or oxygen atom; and Q represents a group of formula

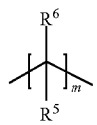

(i)

wherein m is 1 or 2, and $R^5$ and $R^6$ represent, simultaneously or independently, a hydrogen atom, a $C_{1-6}$ linear, branched or cyclic alkyl or a $C_{6-10}$ aromatic group optionally substituted; two distinct $R^6$ and/or $R^5$ groups, taken together, may form a $C_{3-8}$ saturated ring optionally substituted, including the atoms to which said $R^6$ and/or $R^5$ groups are bonded, and optionally containing one or two additional nitrogen or oxygen atoms.

According to an embodiment, by "aromatic group or ring" it is meant a phenyl or naphthyl group.

As mentioned above, in said ligand (B) the atoms which may coordinate the Ru atom are the two N atoms bearing the $R^1$ groups. Therefore, it is also understood that whenever said $R^1$, $R^2$, $R^3$, $R^5$, $R^6$ or any other group comprises heteroatoms such as N or O, said heteroatoms are not coordinating.

Possible optional substituents of $R^1$, $R^2$, $R^3$, $R^5$, $R^6$ are one, two, three or four groups selected amongst i) halogens (in particular when said substituents are on aromatic moieties), ii) $C_{1-6}$ alkoxy, alkyl, alkenyl, or iii) a benzyl group or a fused or non-fused phenyl group, said group being optionally substituted by one, two or three halogen, $C_{1-8}$ alkyl, alkoxy, amino, nitro, ester, sulfonate or halo- or perhalo-hydrocarbon groups.

For the sake of clarity, and as mentioned above, in any one of the embodiments of the present invention, whenever two groups of formula (B) are taken together to form a cycle or ring, said cycle or ring can be a mono or bi-cyclic group.

According to any one of the invention's embodiments of said bidentate NN ligand, each $R^1$, simultaneously or independently, represents a hydrogen atom or a $C_{1-4}$ linear or branched alkyl group.

According to any one of the invention's embodiments of said bidentate NN ligand, at least one $R^1$ represents a hydrogen atom, or even the two $R^1$ represent a hydrogen atom.

According to any one of the invention's embodiments of said bidentate NN ligand, $R^2$ and $R^3$, taken separately, represent, simultaneously or independently, a hydrogen atom, a $C_{1-4}$ linear or branched alkyl group or a phenyl group optionally substituted; a $R^1$ and an adjacent $R^2$, taken together, may form a saturated or aromatic heterocycle containing 5 or 6 atoms and including the atoms to which said $R^1$ and $R^2$ are bonded and optionally containing one additional oxygen atom; two $R^2$, taken together, may form a saturated or unsaturated ring having 5 or 6 atoms and including the atoms to which said $R^2$ or $R^3$ groups are bonded, said ring being optionally substituted and optionally containing one additional oxygen atom.

According to any one of the invention's embodiments of said bidentate NN ligand, $R^2$ and $R^3$, taken separately, represent, simultaneously or independently, a hydrogen atom, a $C_{1-4}$ linear or branched alkyl group; a $R^1$ and an adjacent $R^2$, taken together, may form a saturated or aromatic heterocycle containing 6 atoms and including the atoms to which said $R^1$ and $R^2$ are bonded; two $R^2$, taken together, may form a saturated or unsaturated ring having 5 or 6 atoms and including the atoms to which said $R^2$ or $R^3$ groups are bonded.

According to any one of the invention's embodiments of said bidentate NN ligand, said Q represents a group of formula

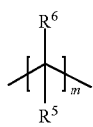

(i)

wherein m is 1 or 2, and
$R^5$ and $R^6$ represent, simultaneously or independently, a hydrogen atom, a $C_{1-4}$ linear or branched alkyl group or a phenyl group optionally substituted.

According to any one of the invention's embodiments of said bidentate NN ligand, said $R^5$ and $R^6$ represent, simultaneously or independently, a hydrogen atom, or a $C_{1-4}$ linear alkyl group.

According to a particular embodiment of the invention, said Q can be a group of formula (i) wherein m is 1 or 2, $R^5$ is a hydrogen atom and $R^6$ is as defined above.

According to any one of the invention's embodiments of said bidentate NN ligand, said ligand NN is represented by formula

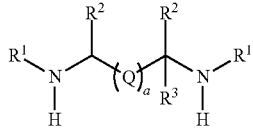

(B')

wherein a represents 0 or 1;
each $R^1$, simultaneously or independently, represents a hydrogen atom or a $C_{1-4}$ linear or branched alkyl group or a benzyl group optionally substituted;
$R^2$ and $R^3$, taken separately, represent, simultaneously or independently, a hydrogen atom, a $C_{1-4}$ linear or branched alkyl group optionally substituted or a phenyl group optionally substituted; a $R^1$ and an adjacent $R^2$, taken together, may form a saturated heterocycle containing 6 atoms and including the atoms to which said $R^1$ and $R^2$ are bonded, and being optionally substituted; two $R^2$ taken together, may form a saturated ring having 5 to to 6 atoms and including the carbon atoms to which said $R^2$ groups are bonded; and
Q represents a group of formula

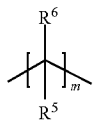

(i)

wherein m is 1 or 2, and
$R^5$ and $R^6$ represent, simultaneously or independently, a hydrogen atom, a $C_{1-4}$ linear or branched alkyl group or a phenyl group optionally substituted.

According to a particular aspect of the above embodiment, said ligand NN of formula (B') is one wherein a represents 0 or 1;
each $R^1$, simultaneously or independently, represents a hydrogen atom or a $C_{1-4}$ linear alkyl group;
$R^2$ and $R^3$, taken separately, represent, simultaneously or independently, a hydrogen atom; two $R^2$ taken together, may form a saturated ring having 5 to 6 atoms and including the carbon atoms to which said $R^2$ groups are bonded; and
Q represents a group of formula

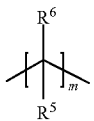

(i)

wherein m is 1 or 2, and
$R^5$ and $R^6$ represent, simultaneously or independently, a hydrogen atom, a $C_{1-4}$ linear alkyl group.

According to any one of the invention's embodiments of said bidentate NN ligand, said ligand NN is represented by formula

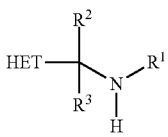

(B")

wherein $R^1$ represents a hydrogen atom or a $C_{1-4}$ linear or branched alkyl group;
$R^2$ and $R^3$, taken separately, represent, simultaneously or independently, a hydrogen atom, a $C_{1-4}$ linear or branched alkyl group; and
HET represents a 2-pyridinyl group optionally substituted by one, two or three $C_{1-4}$ linear or branched alkyl groups or by a benzyl group or a fused or non-fused phenyl or indanyl group, said group being optionally substituted by one, two or three halogen, $C_{1-4}$ alkyl, alkoxy, amino, nitro, ester or sulfonate groups, such as a 2-pyridyl, 2-quinolinyl or a methyl-2-pyridinyl.

According to a particular embodiment of formula (B"), $R^1$ represents, a hydrogen atom.

According to a particular embodiment of formula (B"), $R^2$ and $R^3$, taken separately, represent, simultaneously or independently, a hydrogen atom.

According to a particular embodiment of formula (B"), HET represents a 2-pyridinyl group optionally substituted by one, two or three $C_{1-4}$ linear or branched alkyl groups or a fused or non-fused phenyl group, such as a 2-pyridyl, 2-quinolinyl or a methyl-2-pyridinyl.

According to any one of the invention's embodiments of said bidentate NN ligand, the possible substituents of $R^1$, $R^2$, $R^3$, $R^5$ or $R^6$ of formulae (B), (B') or (B") are one or two i) halogens, ii) $C_{1-5}$ alkyl or alkoxy groups, or iii) a fused or non-fused phenyl group, said group being optionally substituted by one, two or three halogen, $C_{1-4}$ alkyl or alkoxy groups.

According to any one of the above-mentioned embodiments, the N—N ligand is of formula (B').

As non limiting examples of N—N ligands one can cite the ones in the following Scheme (A):

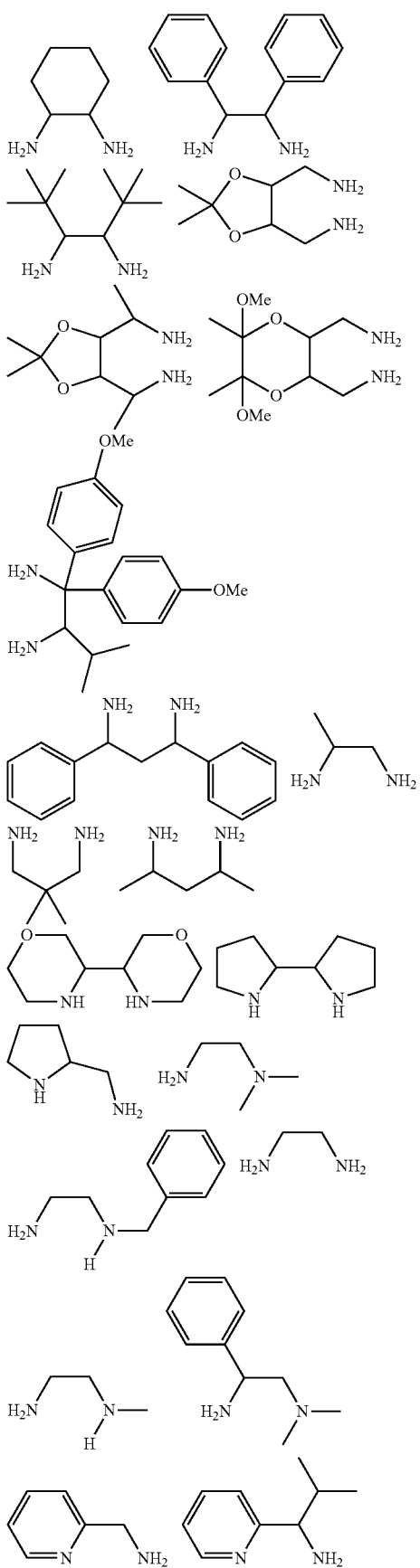

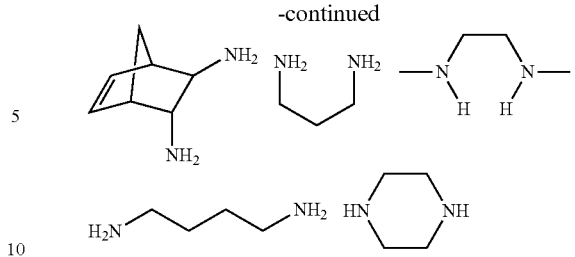

said compounds being in an optically active form or in a racemic form, if applicable.

According to any one of the embodiments of the present invention, the bidentate ligand (PP) can be a compound of formula

(C)

wherein $R^{11}$ and $R^{12}$, when taken separately, represent, simultaneously or independently, a $C_{3-6}$ branched or cyclic alkyl group or a $C_{6-10}$ aromatic group optionally substituted; and Q' represents
a group of formula

(i')

wherein m' is 1, 2, 3 or 4 and
$R^{5'}$ and $R^{6'}$ represent, simultaneously or independently, a hydrogen atom, a $C_{1-6}$ linear or branched alkyl group or a $C_{6-10}$ aromatic group optionally substituted; two distinct $R^{6'}$ and/or $R^{5'}$ groups, taken together, may form a $C_3$ to $C_8$ saturated or unsaturated ring optionally substituted, including the atoms to which said $R^{6'}$ and/or $R^{5'}$ groups are bonded, and optionally containing one or two additional nitrogen or oxygen atoms; or
a $C_{10}$-$C_{16}$ metallocenediyl, a 2,2'-diphenyl, a 1,1'-binaphthalene-2,2'-diyl, a to benzenediyl, a naphthalenediyl, 2,3-bicyclo[2:2:1]hept-5-enediyl, 4,6-phenoxazinediyl, 4,5-(9,9-dimethyl)-xanthenediyl, or bis(phen-2-yl)ether group optionally substituted.

As mentioned above, according to a particular embodiment of the invention, by "aromatic group or ring" for (PP) it is also meant a phenyl or naphthyl derivative.

As mentioned above, in said ligand (C) the atoms which may coordinate the Ru atom are the P atoms of the $PR^{11}R^{12}$ groups. Therefore, it is also understood that whenever said $R^{5'}$, $R^{6'}$, $R^{11}$, $R^{12}$, Q' or any other group comprises heteroatoms such as N or O, said heteroatoms are not coordinating.

Possible substituents of $R^{5'}$, $R^{6'}$, $R^{11}$ and $R^{12}$ are one to five halogens (in particular when said substituents are on aromatic moieties), or one, two or three i) $C_{1-6}$ linear or branched alkyl, alkoxy groups or halo- or perhalo-hydrocarbon, amine groups, ii) $COOR^h$ wherein $R^h$ is a $C_{1-6}$ linear, branched or cyclic alkyl group, iii) $NO_2$ group, or iv) a benzyl group or a fused or non-fused phenyl group, said group being optionally substituted by one, two or three halogen, $C_{1-8}$ alkyl, alkoxy, amino, nitro, ester, sulfonate or halo- or perhalo-hydrocarbon groups. By "halo- or perhalo-hydrocarbon" it is meant groups such as $CF_3$ or $CClH_2$ for instance.

For the sake of clarity, and as mentioned above, in any one of the embodiments of the present invention, whenever two groups of formula (C) are taken together to form a cycle or ring, said cycle or ring can be a mono or bi-cyclic group.

According to any one of the invention's embodiments of said bidentate PP ligand, $R^{11}$ and $R^{12}$, when taken separately, represent, simultaneously or independently, a $C_{3-6}$ cyclic alkyl group or a $C_{6-10}$ aromatic group, or preferably a phenyl group, optionally substituted.

According to any one of the invention's embodiments of said bidentate PP ligand, $R^{11}$ and $R^{12}$ represent each, simultaneously or independently, a $C_{4-6}$ branched or cyclic alkyl group or a phenyl group optionally substituted.

According to any one of the invention's embodiments of said bidentate PP ligand, Q' represents
a group of formula

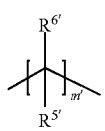

(i')

wherein m' is 1, 2, 3 or 4 and
$R^{5'}$ and $R^{6'}$ represent, simultaneously or independently, a hydrogen atom, a $C_{1-4}$ linear or branched alkyl group or a $C_{6-10}$ aromatic group, or preferably a phenyl group, optionally substituted; two distinct $R^{6'}$ and/or $R^{5'}$ groups, taken together, may form a $C_{4-6}$ saturated or unsaturated ring optionally substituted, including the atoms to which said $R^{6'}$ and/or $R^{5'}$ groups are bonded; or
a $C_{10}$-$C_{16}$ metallocenediyl, a 2,2'-diphenyl, a benzenediyl, a naphthalenediyl, a 1,1'-binaphthalene-2,2'-diyl, 2,3-bicyclo[2:2:1]hept-5-enediyl, 4,6-phenoxazinediyl, 4,5-(9,9-dimethyl)-xanthenediyl or bis(phen-2-yl)ether group optionally substituted.

According to any one of the invention's embodiments of said bidentate PP ligand, Q' may represent a linear $C_{1-5}$ alkanediyl radical, a 1,2- or 1,1'-$C_{10-12}$ metallocenediyl, a 2,2'-diphenyl, a 1,2-benzenediyl, a 1,1'-binaphthalene-2,2'-diyl, or a 1,8- or 1,2-naphthalenediyl or a 4,5-(9,9-dimethyl)-xanthenediyl group optionally substituted.

According to a particular embodiment of the invention, said PP ligand is a compound of formula (C) wherein $R^{11}$ and $R^{12}$ represent, simultaneously or independently, a $C_{4-6}$ branched or cyclic alkyl group or a phenyl group optionally substituted; and
Q' represents a $C_1$-$C_4$ alkanediyl radical optionally substituted, a $C_{10}$-$C_{12}$ ferrocenediyl, a 2,2'-diphenyl, a 1,1'-binaphthalene-2,2'-diyl, a 1,2-benzenediyl or a naphthalenediyl group.

According to any one of the invention's embodiments of said bidentate PP ligand, said ligand is a compound wherein one, two or three of the Q', $R^{11}$ and $R^{12}$ groups are saturated groups (i.e. alkyl or alkanediyl groups). In particular Q' represents a $C_1$-$C_4$ alkanediyl radical optionally substituted and/or $R^{11}$ and $R^{12}$ a branched or cyclic alkyl group.

Possible substituents of said $R^{11}$ or $R^{12}$ are as described above for $R^1$ to $R^6$. Possible substituents of said Q' are as described above for Q.

As non limiting examples of PP ligands, one can cite the ones in the following Scheme (B):

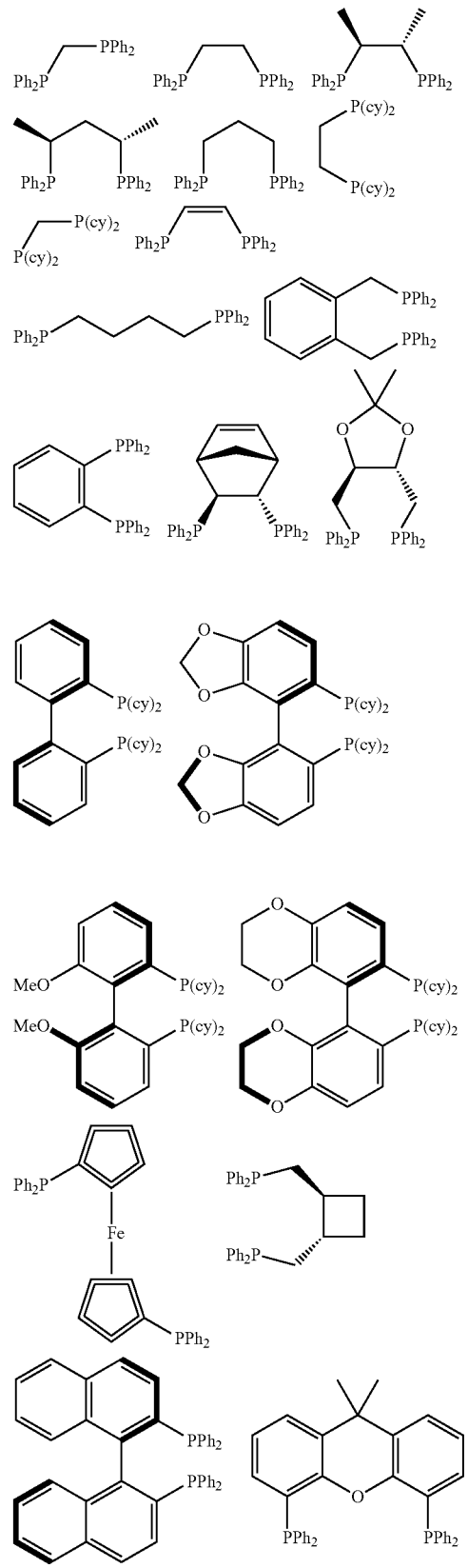

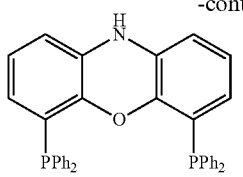

said compounds being in an optically active form or in a racemic form, if applicable, and wherein Ph represents a phenyl group and cy represents a C$_{5-6}$ cycloalkyl group. It is also understood that in the above diphosphines, one may replace cy group by a Ph group or vice versa.

The ligands described above can be obtained by applying standard general methods which are well known in the state of the art and by the person skilled in the art. Many of said ligands NN or PP are even commercially available.

The complexes of formula (1) are generally prepared and isolated prior to their use in the process as exemplified in the Examples herein below but can also be generated to directly in situ from the same precursor [(COD)Ru(RCOO)$_2$]$_n$ (described in the International application No PCT/IB2011/052108) using one equivalent of NN and PP ligands respect to ruthenium or from (NN)(COD)Ru(RCOO)2 complexes using one equivalent of PP ligand respect to ruthenium. In addition, said complexes (1) can also be generated in situ from the known diamine diphosphine ruthenium complex derivatives (PP)(NN)Ru(X)(Y), such as di-acetate, di-propionate, di-alkoxyde (di-isopropoxyde for example), hydridoborohydrido, cationic monoacetate or dicationic (or a mix of those) complexes by adding an excess of an acid RCOOH wherein R has the meaning provided in formula (1). The said complexes (1) can also be generated in situ from the known diamine diphosphine chlorinated ruthenium complex derivatives (PP)(NN)Ru(Cl)(Y) such as dichloride or cationic monochloride complexes by adding an excess of an acid RCOOH wherein R has the meaning provided in formula (1), optionally in the presence of a stoechiometric amount of a silver salt (AgOCOCH$_3$, AgBF$_4$, AgPF$_6$, AgOSO$_2$CF$_3$ for example) with respect to chloride atoms.

The invention complexes of formula (1) are novel, to the best of our knowledge. Therefore such complex (1) is also an object of the present invention.

As previously mentioned, the processes may comprise the addition of an acidic additive. Said additive has the astonishing effect of increasing the speed and sometimes also the yield of the reaction.

Said acidic additive may be selected amongst the weak protic acids, i.e. compounds capable of releasing protons and having a pK$_a$ comprised between 2 and 11.

In particular said acidic additive can be selected amongst:
a carboxylic acid of formula RCOOH, wherein R is as defined above in formula (1); and
phenol (C$_6$H$_5$OH) and a phenol substituted by one or two, or up to five, halogen atoms and/or C$_{1-4}$ alkyl or alkoxyl groups and/or nitro groups and/or carboalkoxy groups.

According to any embodiments of the present invention, said acidic additive can be selected amongst:
a carboxylic acid of formula RCOOH, wherein R is as defined above in formula (1); or
phenol (C$_6$H$_5$OH) and a phenol substituted by one to five halogen atoms and/or by one or two C$_{1-4}$ alkyl or alkoxyl groups and/or nitro groups and/or carboalkoxy groups.

According to any embodiments of the present invention, said carboxylic acid has a pK$_a$ comprised between 3 and 5.5. Similarly, according to any embodiments of the present invention, said substituted or unsubstituted phenol has a pK$_a$ comprised between 5 and 10.5.

As non limiting examples of said acidic additive, one may cite the following: diphenylphosphonic acid, hexylboronic acid, 4-NO$_2$-phenol, 4-carbomethoxyphenol, 4-OMe-phenol, pentafluorophenol, isobutyric acid, sec-butyric acid, pivalic acid, $^t$Bu-acetic acid, 2-Et-hexanoic acid, cyclohexanecarboxylatic acid, picolinic acid, cinnamic acid, benzoic acid, 2,4,6-trimethyl-benzoic acid, 4-Me-benzoic acid, 4-NO$_2$-benzoic acid, 4-OMe-benzoic acid, 3,5-diCl-benzoic acid, 2,4-diCl-benzoic acid, 1-adamantane carboxylic acid or isovaleric acid.

The said acidic additive can be added as such into the reaction medium or, as in the case of the carboxylic acids, can be generated in situ, e.g. by adding a carboxylic anhydride and optionally an alcohol.

As previously mentioned, the processes of the invention consist in the hydrogenation of a substrate using a ruthenium complex in the absence of a base. A typical process implies the mixture of the substrate with the ruthenium complex, and optionally a solvent and an acidic additive, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 1 ppm to 10000 ppm relative to the amount of substrate. Preferably, the complex concentration will be comprised between 10 ppm to 2000 ppm. It goes without saying that the optimum concentration of complex will depend, as the person skilled in the art knows, on the nature of the latter, on the nature and quality of the substrate, on the nature of the solvent used if any, on the reaction temperature and on the pressure of H$_2$ used during the process, as well as the desired time of reaction.

Useful quantities of acidic additive, added to the reaction mixture, may be comprised in a relatively large range. One can cite, as non-limiting examples, ranges between 1 to 10000 molar equivalents, relative to the complex of formula (1), preferably 10 to 2000 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include C$_{6-10}$ aromatic solvents such as toluene or xylene; C$_{5-12}$ hydrocarbon solvents such as hexane or cyclohexane; C$_{4-8}$ ethers such as tetrahydrofuran or MTBE; C$_{4-10}$ esters such as ethyl acetate; C$_{1-2}$ chlorinated hydrocarbon, such as dichloromethane;

C$_{2-6}$ primary or secondary alcohols, such as isopropanol or ethanol; C$_{2-6}$ polar solvents such as DMF, acetonitrile, DMSO, acetone; or mixtures thereof. In particular said solvent can be an apolar aprotic solvent such as an aromatic solvent or a hydrocarbon solvent. The choice of the solvent is a function of the nature of the complex and the substrate, and the person skilled in the art is well able to select the solvent most convenient in each case to optimize the hydrogenation reaction.

In the hydrogenation process of the invention, the reaction can be carried out at a H$_2$ pressure comprised between 10$^5$ Pa and 80×10$^5$ Pa (1 to 100 bars) or even more if desired. Again, a person skilled in the art is well able to adjust the pressure as a function of the catalyst load and of the dilution of the substrate in the solvent. As examples, one can cite typical pressures of 1 to 50×10$^5$ Pa (5 to 50 bars).

The temperature at which the hydrogenation can be carried out is comprised between 0° C. and 200° C., more preferably in the range of between 50° C. and 150° C. Of course, a person skilled in the art is also able to select the preferred temperature as a function of the melting and boiling point of the starting and final products as well as the desired time of reaction or conversion.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in stainless steel autoclave. $H_2$ gas (99.99990%) was used as received. All substrates and solvents were distilled from appropriate drying agents under Ar. NMR spectra were recorded on a Bruker AM-400 ($^1H$ at 400.1 MHz, $^{13}C$ {$^1H$} at 100.6 MHz, and $^{31}P$ at 161.9 MHz) spectrometer and normally measured at 300 K, in $CD_2Cl_2$ unless indicated otherwise. Chemical shifts are listed in ppm.

Example 1

Preparation of Complexes of Formula (1)

The invention complexes were synthesized in one or two steps going through the corresponding [Ru(Diene)(NN)(RCOO)$_2$](diene)(diamine)ruthenium(biscarboxylate) derivative, this one being isolated or not (by "Diene" it is meant here a cyclooctadiene (COD) in particular).

Two Step Procedure:

A) The [Ru(diene)(RCOO)$_2$] (in general [Ru(COD)(RCOO)$_2$], see the application PCT/IB2011/052108) precursor was loaded into a schlenck tube. It was then purged with three vacuum-nitrogen cycles. Degazed 30/50 petroleum ether was then added to generally afford a suspension. Diamine (1 eq./Ru) was then added slowly to the stirred suspension generally leading to an immediate change in color of both the solution and the solid. After stirring at mild temperature (25-60° C.) under nitrogen for several hours (temperature and duration depending on nature of diamine ligand), the solid was generally filtered under nitrogen, washed several times with degazed 30/50 petroleum ether and then dried under vacuum to afford the desired corresponding [Ru(Diene)(NN)(RCOO)$_2$] complex in generally more than 80 mol.% yields as cis or trans isomer or cis/trans isomers mixture (carboxylate in cis and trans position).

(Ethylenediamine)(1,5-cyclooactodiene)Ru(pivalate)$_2$ $^{13}C$ NMR (one isomer only): 188.59 (C), 89.80 (CH), 43.56 (CH$_2$), 40.78 (C), 29.26 (CH$_2$), 28.48 (CH$_3$).

(Ethylenediamine)(1,5-cyclooactodiene)Ru(adamantane-1-carboxylate)$_2$ $^{13}C$ NMR (one isomer only): 187.84 (C), 89.62 (CH), 43.54 (CH$_2$), 42.95 (C), 40.71 (CH$_2$), 37.40 (CH$_2$), 29.87 (CH).

(Piperazine)(1,5-cyclooactodiene)Ru(pivalate)$_2$ $^{13}C$ NMR (one isomer only): 193.74 (C), 100.23 (CH), 77.5 (CH), 48.56 (CH$_2$), 48.02 (CH$_2$), 47.51 (CH$_2$), 47.04 (CH$_2$), 40.63 (C), 30.45 (CH$_2$), 28.27 (CH$_2$), 27.54 (CH$_3$).

B) The obtained [Ru(Diene)(NN)(RCOO)$_2$] precursor along with disphosphine ligand were loaded together into a schlenck tube. It was then purged with three vacuum-nitrogen cycles. Degazed xylene was then added to generally afford a suspension. The obtained suspension was then heated to 120-140° C. under nitrogen for several hours (temperature and duration depending on nature of the diphosphine ligand) to generally afford a solution that progressively changes in color. It was then cooled down to room temperature and degassed 30/50 petroleum ether was generally slowly added to the mixture for complete product precipitation. After filtration of the remaining solid under nitrogen, it was washed several times with degassed 30/50 petroleum, then with a degassed 30/50 petroleum/acetone mixture. After drying dried under vacuum, desired [Ru(PP)(NN)(RCOO)$_2$] complex was obtained in 50-95 mol.% yield as cis or trans isomer (carboxylate in cis or trans postion) or cis/trans isomers mixture, both stereochemistry and yields mainly depending on the nature of the diphosphine ligand used.

On Step Procedure:

[Ru(Diene)(RCOO)$_2$] precursor was loaded into a schlenck tube. It was then purged with three vacuum-nitrogen cycles. Degassed xylene was then added to generally afford a suspension. Diamine (1 eq./Ru) was then added slowly to the stirred suspension generally leading to an immediate change in color of both the solution and the solid. After stirring at room temperature under nitrogen for several hours, diphoshine ligand (1 eq./Ru) was added to the reaction mixture and reaction was then heated to 120-140° C. under nitrogen for several hours to generally afford a solution that progressively changes in color. It was then cooled down to room temperature and degassed 30/50 petroleum ether was generally slowly added to the mixture for complete product precipitation. After filtration under nitrogen, the remaining solid was washed several times with degassed 30/50 petroleum, then with a degazed 30/50 petroleum/acetone mixture. After drying dried under vacuum, [Ru(PP)(NN)(RCOO)$_2$] complex was generally obtained in 40-95 mol.% yield as cis or trans isomer (carboxylate in cis or trans postion) or cis/trans isomers mixture, both stereochemistry and yields depending on the nature of the diphosphine ligand used.

Note: the two steps reverse procedure, i.e. initial synthesis of [Ru(PP)(RCOO)$_2$] complexes followed by further reaction with diamine, can also be used.

(Ethylenediamine)[1,1-bis(diphenylphosphino)methane]Ru(pivalate)$_2$ $^{31}P$ NMR: 9.35 (d, J=79.0, 1P cis isomer), 9.84 (s, 2P trans isomer, minor), 25.29 (d, J=79.0, 1P cis isomer).

$^{13}C$ NMR (cis isomer only): 28.30 (CH$_3$), 28.78 (CH$_3$), 39.82 (C), 49.59 (d, J=3.8, C), 41.80 (CH$_2$), 46.33 (d, J=3.6, CH$_2$), 50.62 (t, J=20.2, CH$_2$), 128.05 (d, J=9.7, CH), 128.47 (d, J=9.8, CH), 129.05 (d, J=9.4, CH), 129.31 (d, J=4.6, CH), 129.43 (CH), 130.28 (dd, J=12.5 and 11.5, CH), 131.93 (d, J=12.5, CH), 132.38 (d, J=12.0, CH), 133.34 (d, J=12.5, CH), 135.05 (dd, J=14.5 and 8.0, C), 136.07 (d, J=31.1, C), 137.3 (dd, J=28.2 and 7.5, C), 187.66 (d, 2.4, C), 189.20 (C).

(Ethylenediamine)[1,2-bis(diphenylphosphino)ethane]Ru(pivalate)$_2$ $^{31}P$ NMR: 73.06 (d, J=20.6, 1P cis isomer), 73.90 (s, 2P trans isomer), 88.83 (d, J=20.6, 1P cis isomer).

$^{13}C$ NMR (cis/trans isomers mixture): 26.83 (dd, J=32.2 and 14.5, CH$_2$), 27.53 (t, J=22.0, CH$_2$), 28.48 (CH$_3$), 28.65 (CH$_3$), 28.68 (CH$_3$), 30.68 (dd, J=31.4 and 10.8, CH$_2$), 39.70

(C), 40.08 (C), 40.54 (d, J=4.0, C), 41.51 (d, J=1.8, CH$_2$), 43.48 (CH$_2$), 44.65 (d, 3.6, CH$_2$), 127.88 (d, J=9.6, CH), 128.28 (t, J=4.6, CH), 128.69 (d, J=9.2, CH), 128.92 (d, J=2.4, CH), 129.00 (d, J=8.2, CH), 129.17 (CH), 129.37 (d, J=8.8, CH), 129.62 (dd; J=15.0 and 1.8, CH), 130.27 (d, J=9.2, CH), 130.37 (d, J=2.4, CH), 131.87 (d, J=10.2 Hz; CH), 132.81 (t, J=5.2, CH), 134.39 (d, J=10.2, CH), 134.67 (d, J=10.4, CH), 135.07 (d, J=36.0, C), 136.23 (t, J=36, C), 138.92 (t, J=17.9, C), 139.57 (d, J=37.0, C), 187.43 (d, J=2.4, C), 188.39 (C), 188.50 (C).

(Ethylenediamine)[1,3-bis(diphenylphosphino)propane]Ru(pivalate)$_2$ $^{31}$P NMR: 39.19 (d, J=48.0, 1P cis isomer, minor), 42.04 (s, 2P trans isomer), 60.69 (d, J=48.0, 1P cis isomer, minor),
$^{13}$C NMR (trans isomer only): 19.09 (CH$_2$), 24.96 (t, J=15.7, CH$_2$), 28.82 (CH$_3$), 39.93 (C), 43.96 (CH$_2$), 127.98 (t, J=4.2, CH), 128.87 (CH), 132.96 (t, J=4.5, CH), 138.27 (t, J=17.6, C), 188.65 (C).

(Ethylenediamine)[1,4-bis(diphenylphosphino)butane]Ru(pivalate)$_2$ $^{31}$P NMR: 42.03 (d, J=38.2, 1P cis isomer, minor), 45.97 (s, 2P trans isomer), 60.60 (d, J=38.2, 1P cis isomer, minor).
$^{13}$C NMR (trans isomer only): 22.81 (CH$_2$), 26.31 (t, J=13.3, CH$_2$), 28.65 (CH$_3$), 40.03 (C), 44.02 (CH$_2$), 127.95 (t, J=4.2 Hz; CH), 128.89 (CH), 133.41 (t, J=4.6, CH), 139.51 (dd, J=18.2 and 16.5, C), 185.6 (C).

(Ethylenediamine)[9,9-dimethyl-4,5-bis(diphenylphosphino)xanthene]Ru(pivalate)$_2$ $^{31}$P NMR: 35.89 (s, 2P, cis isomer)
$^{13}$C NMR (cis isomer only): 23.22 (CH$_3$), 27.95 (CH$_3$), 28.62 (CH$_3$), 32.47 (CH$_3$), 36.27 (C), 39.45 (C), 39.97 (C), 44.18 (CH$_2$), 123.43 (t, J=2.4, CH), 125.95 (CH), 127.59 (t, J=4.6, CH), 128.17 (t, J=3.9, CH), 128.66 (CH), 128.93 (CH), 132.16 (CH), 133.95 (t, J=4.6, CH), 134.11 (t, J=3.8, CH), 135.55 (d; J=4.6, C), 135.74 (d, J=5.3, C), 135.90 (d, J=7.6, C), 155.79 (t, J=4.0, C), 189.63 (t, J=1.8, C), 190.35 (C).

(Ethylenediamine) [1,1'-bis(diphenylphosphino)ferrocene]Ru(pivalate)$_2$ $^{31}$P NMR: 41.01 (d, J=37.2, 1P cis isomer, minor), 47.51 (s, 2P trans isomer), 64.04 (d, J=37.2, 1P cis isomer, minor),
$^{13}$C NMR (trans isomer only): 28.64 (CH$_3$), 40.10 (C), 43.62 (CH$_2$), 71.36 (t, J=2.6, CH), 75.37 (t, J=4.1, CH), 83.56 (t, J=23.5, C), 127.75 (t, J=4.4, CH), 129.17 (CH), 134.72 (t, J=5.2, CH), 138.94 (t, J=18.3 Hz), 189.36 (C).

(Ethylenediamine)[1,2-bis(diphenylphosphino)benzene]Ru(pivalate)$_2$ $^{31}$P NMR: 72.60 (d, J=24.2, 1P cis isomer), 75.29 (s, 2P trans isomer, minor), 84.05 (d, J=24.2, 1P cis isomer).
$^{13}$C NMR (cis isomer only): 28.35 (CH$_3$), 28.51 (CH$_3$), 40.23 (C), 40.35 (d, J=3.8, C), 42.17 (d, J=1.8, CH$_2$), 46.43 (d, J=3.6, CH$_2$), 127.83 (d, J=9.6, CH), 128.29 (d, J=8.8, CH), 128.42 (d, J=9.6, CH), 128.87 (d, J=9.6, CH), 129.16 (d, J=2.4, CH), 129.33 (d, J=1.6, CH), 129.48 (dd, J=6.4 and 2.4, CH), 129.61 (dd, J=6.4 and 2.4, CH), 129.90 (d, J=2.4, CH), 130.32 (d, J=2.0, CH), 131.41 (dd, J=14.8 and 1.6, CH), 131.89 (d, J=10.2, CH), 132.35 (d, J=14.4, CH), 133.19 (d, J=10.6, CH), 133.65 (dd, J=33.8 and 8.4, C), 135.71 (d, J=10.8, CH), 136.15 (t, J=20.3, C), 145.39 (d, J=31.8, C), 145.78 (d, J=17.8, C), 146.10 (d, J=19.2, C), 146.52 (d, J=33.0, C), 187.40 (d, J=1.8, C), 188.24 (C).

(Ethylenediamine)[1,2-bis(dicyclohexylphosphino)ethane]Ru(pivalate)$_2$ $^{31}$P NMR: 76.16 (d, J=21.3, 1P cis isomer), 76.37 (s, 2P trans isomer, minor), 78.49 (d, J=21.3, 1P cis isomer).
$^{13}$C NMR (cis isomer only): 20.24 (dd, J=25.6 and 11.6, CH$_2$), 22.01 (dd, J=27.8 and 11.8, CH$_2$), 26.85 (d, J=12.8, CH$_2$), 27.10 (d, J=2.0, CH$_2$), 27.86 (t, J=9.4, CH$_2$), 28.06-28.26 (m, CH$_2$), 28.47 (t, J=11.5, CH$_2$), 28.70 (CH$_3$), 28.95 (d, J=3.8, CH$_2$), 29.06 (CH$_3$), 29.17 (d, J=15.0, CH$_2$), 29.51 (d, J=3.8, CH$_2$), 29.55 (CH$_2$), 29.76 (d, J=3.8, CH$_2$), 29.94 (CH$_2$), 30.47 (CH$_2$), 36.16 (d, J=16.2, CH), 37.67 (d, J=18.8, CH), 39.38 (d, J=18.2, CH), 39.78 (d, J=18.0, CH), 40.10 (C), 40.67 (d, J=3.6, C), 40.75 (CH$_2$), 47.34 (d, J=3.6, CH$_2$), 186.79 (C quat), 188.59 (C).

(trans-Cyclohexane-1,2-diamine)[1,2-bis(diphenylphosphino)ethane]Ru(pivalate)$_2$ $^{31}$P NMR: 73.23 (d, J=21.0, 1P cis isomer), 73.93 (s, 2P trans isomer), 88.99 (d, J=21.0, 1P cis isomer).
$^{13}$C NMR (cis/trans isomers mixture): 25.06 (CH$_2$), 25.29 (CH$_2$), 25.55 (CH$_2$), 26.75 (dd, J=31.0 and 14.6, CH$_2$), 27.69 (t, J=21.6, CH$_2$), 28.48 (CH$_3$), 28.63 (CH$_3$), 28.65 (CH$_3$), 30.26 (dd, J=31.4 and 11.2, CH$_2$), 34.92 (CH$_2$), 36.57 (d, J=2.6, CH$_2$), 36.66 (CH$_2$), 39.61 (C), 40.07 (C), 40.47 (d, J=4.0, C), 55.66 (d, J=1.8, CH), 58.04 (CH), 59.72 (d, J=3.4, CH), 127.84 (d, J=9.0, CH), 127.97 (t, J=4.5, CH), 128.45 (t, J=4.4, CH), 128.81 (dd, J=20.6 and 9.4, CH), 129.14 (t, J=7.0, CH), 129.32 (d, J=8.8, CH), 129.45 (CH), 129.57 (dd, J=14.0 and 2.0, CH), 130.12 (d, J=9.0, CH), 130.36 (d, 2.2, CH), 131.82 (d, J=10.4, CH), 132.40 (t, J=5.2, CH), 133.22 (t, J=5.2, CH), 134.37 (d, J=10.4, CH), 134.75 (d, J=10.4, CH), 134.77 (d, J=35.6, C), 136.04 (d, J=33.6, C), 136.21 (dd; J=36.9 and 1.6, C), 139.80 (d, J=37.0, C), 187.44 (d, J=2.4, C), 188.26 (C), 188.41 (C).

(Pyridin-2-ylmethanamine)[1,2-bis(diphenylphosphino)ethane]Ru(pivalate)$_2$ $^{31}$P NMR: 85.57 (d, J=18.0, 1P cis isomer), 89.65 (d, J=18.0, 1P cis isomer).
$^{13}$C NMR (cis isomer only): 27.06 (dd, J=32.5 and 12.5, CH$_2$), 28.47 (CH$_3$), 28.92 (CH$_3$), 31.17 (dd, J=34.5 and 13.2, CH$_2$), 38.60 (C), 40.58 (d, J=4.4, C), 49.42 (d, J=3.0, CH$_2$), 119.79 (CH); 122.87 (d, J=2.8, CH), 127.66 (d, J=9.6, CH), 127.79 (d, J=9.6, CH), 128.59 (d, J=1.8, CH), 128.89 (dd, J=8.4 and 3.4, CH), 129.35 (dd, J=15.2 and 1.8 Hz), 129.98 (d, J=8.4, CH), 131.08 (d, J=9.4, CH), 133.28 (d, J=9.8, CH), 133.94 (d; J=10.4, CH), 136.47 (CH), 137.95 (d, J=39.6, C), 138.21 (d, J=41.0, C), 140.21 (d, J=35.6, C), 143.16 (d, J=33.8, C), 150.05 (CH), 163.23 (C), 183.57 (C), 188.55 (C).

(Ethylenediamine)[1,2-bis(diphenylphosphino)ethane]Ru(benzoate)$_2$ $^{31}$P NMR: 73.08 (d, J=20.5, 1P cis isomer), 74.33 (s, 2P trans isomer, minor), 89.76 (d, J=20.5, 1P cis isomer).
$^{13}$C NMR (cis isomer only): 27.24 (dd, J=31.2 and 14.5, CH$_2$), 30.94 (dd, J=32.4 and 10.6, CH$_2$), 42.12 (CH$_2$), 45.01 (d, J=3.8, CH$_2$), 127.48 (CH), 127.72 (CH), 127.92 (d, J=9.0, CH), 128.75 (d, J=9.4, CH), 129.17 (d, J=8.8, CH), 129.42 (CH), 129.66 (d, J=2.2, CH), 129.76 (CH), 130.10 (CH), 130.31 (d, J=9.0, CH), 130.55 (d, J=1.8, CH), 131.89 (d, J=10.0, CH), 134.23 (d, J=10.6, CH), 134.58 (d, J=10.6, CH), 135.06 (d, J=24.2, C), 135.91 (t, J=37.8, C), 138.31 (C), 138.50 (d, J=4.8, C), 139.09 (d, J=38.0, C), 176.11 (d, J=1.8, C), 176.47 (C).

(Ethylenediamine)[1,2-bis(diphenylphosphino)ethane]Ru(2,4,6-trimethylbenzoate)$_2$ $^{31}$P NMR: 72.60 (d, J=18.5, 1P cis isomer), 73.53 (s, 2P trans isomer, minor), 90.69 (d, J=18.5 Hz, 1P cis isomer).

$^{13}$C NMR (cis isomer only): 19.82 (CH$_3$), 19.89 (CH$_3$), 21.00 (CH$_3$), 21.12 (CH$_3$), 28.15 (dd, J=30.7 and 14.8, CH$_2$), 30.86 (J=30.6 and 10.8, CH$_2$), 42.53 (CH$_2$), 44.85 (d, J=3.6, CH$_2$), 127.59 (t, J=4.7, CH), 127.80 (CH), 128.88-129.10 (m, CH), 129.55 (CH), 129.64 (d, J=4.6, CH), 130.00 (d, J=1.6, CH), 130.38 (d, J=9.4, CH), 130.78 (d, J=2.2, CH), 132.30 (d, J=10.4, CH), 133.68 (d, J=8.2, C), 134.35 (d, J=9.8, CH), 134.58 (C), 134.72 (C), 134.94 (C), 135.38 (C), 135.51 (d, J=9.8, CH), 135.69 (C), 139.31 (C), 139.41 (d, J=4.1, C), 139.70 (C), 180.38 (d, J=2.6, C), 181.28 (C).

(Ethylenediamine)[1,2-bis(diphenylphosphino)ethane]Ru[(3,3-dimethylbutanoate)$_2$]

$^{31}$P NMR: 72.96 (d, J=19.5, 1P cis isomer), 74.56 (s, 2P trans isomer), 89.90 (d, J=19.5, 1P cis isomer).

$^{13}$C NMR (cis/trans isomers mixture): 27.01 (dd, J=30.6 and 14.4, CH$_2$), 27.86 (t, J=22.3, CH$_2$), 30.16 (CH$_3$), 30.25 (CH$_3$), 30.31 (CH$_3$), 30.39 (C), 30.54 (C), 30.66 (C), 30.82 (dd, J=30.9 and 11.2, CH$_2$), 41.91 (d, J=2.2, CH$_2$), 43.92 (CH$_2$), 44.79 (d, J=3.8, CH$_2$), 53.15 (CH$_2$), 53.37 (d, J=3.6, CH$_2$), 53.68 (CH$_2$), 127.87 (d, J=9.1, CH), 128.23 (t, J=4.5, CH), 128.84 (t, J=8.8, CH), 129.16 (d, J=5.0, CH), 129.33 (d, J=8.4, CH), 129.58 (dd, J=12.2 and 2.4, CH), 130.27 (d, J=9.2, CH), 130.36 (d, J=2.4, CH), 132.15 (d, J=10.0, CH), 132.81 (t, J=4.8, CH), 134.25 (d, J=10.0, CH), 134.92 (d, J=10.8, CH), 135.35 (d, J=35.4, C), 135.99 (t, J=35.0, C), 138.71 (t, J=17.8, C), 139.60 (d, J=37.4, C), 182.18 (d, J=2.5 Hz; C), 183.17 (C), 183.34 (C).

(Ethylenediamine)[1,2-bis(diphenylphosphino)ethane]Ru(adamantane-1-carboxylate)$_2$ $^{31}$P NMR: 72.74 (d, J=20.5, 1P cis isomer), 73.86 (s, 2P trans isomer), 88.64 (d, J=20.5, 1P cis isomer).

$^{13}$C NMR (cis/trans isomers mixture): 26.80 (dd, J=31.4 and 14.5; CH$_2$), 27.64 (t, J=21.8, CH$_2$), 28.92 (CH), 29.19 (CH), 29.32 (CH), 29.42 (CH), 30.68 (dd, J=31.2 and 10.6, CH$_2$), 37.23 (CH$_2$), 37.41 (CH$_2$), 37.51 (CH$_2$), 37.65 (CH$_2$), 39.90 (CH$_2$), 40.48 (CH$_2$), 40.53 (CH$_2$), 40.60 (CH$_2$), 41.54 (d, J=1.8, CH$_2$), 41.84 (C), 42.33 (C), 42.65 (d, J=4.2, C), 43.45 (CH$_2$), 44.66 (d, J=3.8, CH$_2$), 127.91 (d, J=9.4, CH), 128.27 (t, J=4.5, CH), 128.65 (d, J=9.0, CH), 128.87-129.07 (m, CH), 129.16 (CH), 129.35 (d, J=8.8, CH), 129.60 (dd, J=18.6 and 2.0, CH), 130.25 (d, J=9.0, CH), 130.33 (d, J=2.0, CH), 131.85 (d, J=10.0, CH), 132.89 (t, J=5.0, CH), 134.51 (d, J=10.6, CH), 134.72 (d, J=10.8, CH), 135.06 (d, J=36.2, C), 136.23 (t, J=32.6, C), 138.99 (t, J=18.2, C), 139.53 (d, J=37.2, C), 186.98 (d, J=2.6, C), 187.91 (C), 188.02 (C).

[(Ethylenediamine)[(rac.)-2,2'-bis(diphenylphosphino)-1,1'-binaphthalene]Ru(pivalate)$_2$]

$^{31}$P NMR: 46.88 (d, J=35.4, 1P cis isomer, minor), 47.97 (s, 2P trans isomer), 60.08 (d, J=35.4, 1P cis isomer, minor).

$^{13}$C NMR (trans isomer only): 28.89 (CH$_3$), 39.95 (C), 43.39 (CH$_2$), 124.95 (CH), 125.69 (broad s, CH), 125.91 (CH), 126.72 (t, J=4.6, CH), 127.39 (broad s, CH), 127.42 (CH), 127.85 (CH), 127.95 (t, J=4.0, CH), 129.05 (CH), 133.51 (C), 134.35 (C), 135.24 (dt, J=33.6 and 4.4, CH), 137.46 (t, J=16.3, C), 139.52 (t, J=8.6, C), 139.70 (t, J=18.1, C), 188.49 (C).

(Ethylenediamine)[bis(2-diphenylphosphinophenyl)ether]Ru(pivalate)$_2$ $^{31}$P NMR: 44.12 (s, 2P trans isomer).

(Ethylenediamine)[(rac.)-trans-1,2-bis((diphenylphosphino)methyl)cyclobutane Ru(pivalate)$_2$]

$^{31}$P NMR: 39.98 (s, 2P trans isomer).

$^{13}$C NMR (trans isomer only): 27.18 (t, J=6.8, CH$_2$), 28.68 (CH$_3$), 36.06 (t, J=12.2, CH$_2$), 38.82 (broad s, CH), 39.99 (C), 44.00 (CH$_2$), 39.95 (C), 43.39 (CH$_2$), 124.95 (CH), 125.69 (broad s, CH), 125.91 (CH), 126.72 (t, J=4.6, CH), 127.39 (broad s, CH), 127.42 (CH), 127.85 (CH), 127.95 (t, J=4.0, CH), 129.05 (CH), 133.51 (C), 134.35 (C), 135.24 (dt, J=33.6 and 4.4, CH), 137.46 (t, J=16.3, C), 139.52 (t, J=8.6, C), 139.70 (t, J=18.1, C), 188.49 (C).

(Ethylenediamine)[(rac.)-trans-5,6-bis(diphenylphosphino)bicyclo[2.2.1]hept-2-ene]Ru(pivalate)$_2$]

$^{31}$P NMR: 37.30 (d, J=36.0, 1P isomer 1), 37.86 (d, J=36.0, 1P isomer 2), 45.85 (d, J=35.0, 1P isomer 3), 49.27 (d, J=35.0, 1P isomer 3), 61.34 (d, J=36.0 Hz, 1P isomer 1), 62.44 (d, J=36.0, 1P isomer 2).

(Ethylenediamine)[bis(dicyclohexylphosphino)methane]Ru(pivalate)$_2$ $^{31}$P NMR: 22.17 (s, 2P trans isomer).

$^{13}$C NMR (trans isomer): 26.70 (CH$_2$), 27.99 (dd, J=11.2 and 6.0, CH$_2$), 28.03 (CH$_2$), 28.89 (CH$_3$), 29.15 (broad s, CH$_2$), 29.64 (CH$_2$), 36.74 (t, J=7.6, CH), 37.11 (t, J=14.6, CH$_2$), 39.93 (C), 43.24 (CH$_2$), 189.44 (C).

(N-Methylethylenediamine)[bis(dicyclohexylphosphino)methane]Ru(pivalate)$_2$ $^{31}$P NMR: 15.18 (d, J=54.9, 1P cis isomer), 22.41 (d, J=54.9, 0.1P cis isomer).

$^{13}$C NMR (cis isomer only): 26.43 (CH$_2$), 26.75 (t, J=13.2, CH$_2$), 27.81 (CH$_2$), 28.03 (dt=12.9 and 4.0, CH$_2$), 28.13 (CH$_2$), 28.22 (t, J=2.4, CH$_2$), 28.73 (CH$_2$), 28.77 (d, J=2.2, CH$_2$), 28.92 (CH$_3$), 29.15 (CH$_3$), 29.51 (d, J=2.2, CH$_2$), 29.55 (CH$_2$), 29.64 (d, J=3.6, CH$_2$), 29.89 (D, J=2.4, CH$_2$), 30.29 (d, J=3.2, CH$_2$), 30.62 (d, J=1.6, CH$_2$), 35.92 (d, J=9.0, CH), 36.71 (t, J=15.2, CH$_2$), 36.91 (t, J=7.2, CH), 37.03 (d, J=16.0, CH), 38.69 (dd, J=9.0 and 7.0, CH), 40.02 (C), 40.15 (C), 41.69 (CH$_3$), 44.17 (broad s, CH$_2$), 53.97 (CH$_2$), 189.61 (C), 190.05 (d, J=1.6, C).

(propane-1,3-diamine)[1,2-bis(diphenylphosphino)ethane]Ru(pivalate)$_2$ $^{31}$P NMR: 78.30 (d, J=20.8, 1P cis isomer), 86.56 (d, J=20.8, 1P cis isomer).

$^{13}$C NMR (cis isomer): 26.19 (dd, J=31.6 and 12.8, CH$_2$), 28.57 (CH$_2$), 28.61 (CH$_3$), 28.76 (CH$_3$), 32.43 (dd, J=32.3 and 12.5, CH$_2$), 39.72 (C), 40.45 (d, J=3.9, C), 41.07 (CH$_2$), 42.45 (CH$_2$), 127.85 (d, J=9.5, CH), 128.25 (d, J=9.1, CH), 129.00 (d, J=8.2, CH), 129.08 (broad s, CH), 129.15 (d, J=8.2, CH), 129.40 (d, J=1.3, CH), 129.72 (d, J=2.1, CH), 129.83 (d, J=1.5, CH), 131.27 (d; J=8.9, CH), 131.95 (d, J=9.1, CH), 133.72 (d, J=10.5, CH), 134.52 (d, J=10.6, CH), 135.60 (d, J=32.9, C), 136.65 (d, J=37.9 Hz; C), 137.67 (d, J=37.8, C), 140.88 (d, J=35.9, C), 186.55 (C), 188.10 (C).

(2,2-dimethylpropane-1,3-diamine)[1,2-bis(diphenylphosphino)ethane]Ru(pivalate)$_2$ $^{31}$P NMR: 74.92 (d, J=18.5, 1P cis isomer), 82.90 (d, J=18.5, 1P cis isomer).

$^{13}$C NMR (cis isomer): 21.87 (CH$_3$), 26.54 (dd, J=30.2 and 13.0, CH$_2$), 27.99 (CH$_3$), 28.54 (CH$_3$), 28.73 (CH$_3$), 32.41 (dd, J=31.9 and 11.9, CH$_2$), 34.11 (C), 40.12 (C), 40.41 (d, J=3.8, C), 50.15 (CH$_2$), 52.97 (CH$_2$), 127.85 (d, J=9.4, CH), 128.38 (d, J=9.1, CH), 128.91 (broad s, CH), 128.98 (d, J=8.4, CH), 129.60 (d, J=8.4, CH), 129.66 (broad s, CH), 129.75 (d, J=1.6, CH), 129.99 (d, J=1.6, CH), 131.2 (d, J=9.1, CH), 132.50 (d; J=9.5, CH), 133.67 (d, J=33.6, C), 134.05 (d, J=10.3, CH), 134.53 (d, J=10.5 Hz; CH), 136.23 (d, J=36.2, C), 136.46 (d, J=36.2, C), 141.90 (d, J=35.2, C), 187.93 (C), 188.07 (d, J=1.6, C).

(butane-1,4-diamine)[1,2-bis(diphenylphosphino)ethane]Ru(pivalate)$_2$ $^{31}$P NMR: 76.71 (s, 2P trans isomer).

$^{13}$C NMR (trans isomer): 20.73 (t, J=18.4, CH$_2$), 27.75 (CH$_3$), 28.65 (CH$_2$), 38.00 (C), 40.26 (CH$_2$), 128.29 (t, J=5.6, CH), 128.74 (CH), 132.75 (t, J=27.5, C), 133.42 (t, J=5.0, CH), 180.18 (C).

(butane-1,4-diamine)[1,4-bis(diphenylphosphino)butane]Ru(pivalate)$_2$ $^{31}$P NMR: 62.61 (s, 2P trans isomer).

$^{13}$C NMR (cis isomer): 23.84 (CH$_2$), 27.04 (CH$_3$), 28.49 (t, J=15.0, CH$_2$), 29.34 (CH$_2$), 39.79 (C), 43.02 (CH$_2$), 128.22 (t, J=4.6, CH), 129.46 (CH), 133.07 (t, J=4.3, CH), 137.95 (t, J=20.8, C), 195.21 (C).

In some cases, pure cis and pure trans isomers of [Ru(PP)(NN)(RCOO)$_2$] complex have been isolated by selective crystallisation and afforded similar results in hydrogenation reaction concerning both catalytic activity and reactivity. Also, no information was given concerning stereochemistry of [Ru(PP)(NN)(RCOO)$_2$] catalysts used in following reported hydrogenation results.

Example 2

Catalytic Hydrogenation of Aldehydes Using the Invention's Process: Comparative Example with Various Prior Art Catalysts Influence of Nature of Ruthenium Precursor on Catalytic Activity in 3,7-dimethyloct-6-enal (Citronellal) Selective Hydrogenation

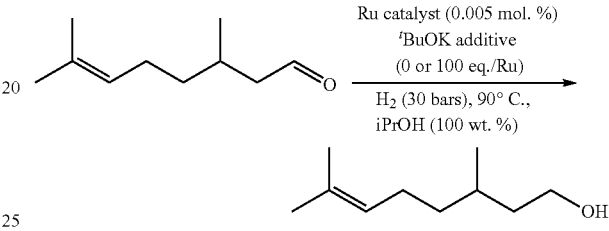

General Procedure: 3,7-dimethyloct-6-enal (8.4 g, 0.05 mol), isopropanol (8.4 g, 100 wt. %), ruthenium catalyst (0.0025 mmol, 0.005 mol.%) and, whenever required tBuOK as additive (28 mg, 0.25 mmol, 0.5 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 30 bars hydrogen. It was then heated to 90° C. and hydrogen pressure was maintained to 30 bars for several hours. Upon reaction completion or after 24 h, autoclave was then cooled down to 25° C. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and yield was calculated based on GC purity of distilled product.

| Complex | Time[1] | Conv.[2] | Yield[3] | Remarks |
|---|---|---|---|---|
| * (En)(dppe)RuCl$_2$ | 24 | 0 | 0 | no tBuOK added |
| * (En)(dppe)RuCl$_2$ | 24 | 100 | 2 | 100 eq. tBuOK/Ru 95 wt. % residues |
| * (En)(dppe)RuCl$_2$ | 24 | 40 | 5 | 100 eq. tBuOK/Ru 35 wt. % residues [4] |
| * (En)(dppe)Ru(H)Cl | 24 | 0 | | no tBuOK added |
| * (En)(dppe)Ru(H)Cl | 24 | 100 | 5 | 100 eq. tBuOK/Ru 90 wt. % residues |
| * (En)(dppe)Ru(H)Cl | 24 | 50 | 10 | 100 eq. tBuOK/Ru 40 wt. % residues [4] |
| * (En)(dppe)Ru(H)(HBH$_3$) | 24 | 10 | 10 | no tBuOK added |
| * (En)(dppe)Ru(H)(HBH$_3$) | 24 | 20 | 20 | no tBuOK added [4] |
| * [(En)(dppe)(OAc)][BF$_4$] | 24 | 20 | 20 | no tBuOK added |
| * [(En)(dppe)][BF$_4$]$_2$ | 24 | 15 | 15 | no tBuOK added |
| * (En)(dppe)Ru(OAc)$_2$ | 24 | 20 | 20 | no tBuOK added |
| * (En)(dppe)Ru(OCOC$_2$H$_5$)$_2$ | 24 | 22 | 22 | no tBuOK added |
| * (En)(dppe)Ru(OCOCF$_3$)$_2$ | 24 | 18 | 16 | no tBuOK added |
| (En)(dppe)Ru(OCO$^t$Bu)$_2$ | 4 | 100 | 98 | no tBuOK added |
| (En)(dppe)Ru(OCOC$_6$H$_5$)$_2$ | 3 | 100 | 98 | no tBuOK added |

[1] In hours
[2] Conversion of the starting aldehyde in % (GC)
[3] Isolated yield of the primary alcohol obtained (mol. %)
En: ethylenediamine; dppe: 1,2-bis(diphenylphosphino)ethane.
* catalyst of the prior art and not being of formula (1)

Influence of Nature of Ruthenium Precursor on Catalytic Activity in 2-methyl-4-((R)-2,2,3-trimethylcyclopent-3-en-1-yl)pent-4-enal Selective Hydrogenation

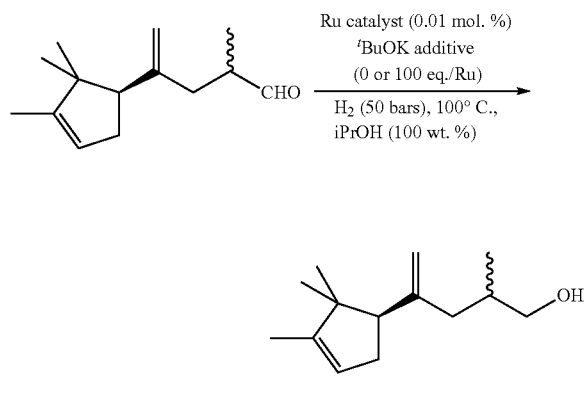

General Procedure: 2-methyl-4-((R)-2,2,3-trimethylcyclopent-3-en-1-yl)pent-4-enal (as a 40/60 (2S,4R)/(2R,4R) diastereoisomers mixture) (10.3 g, 0.05 mol), isopropanol (10.3 g, 100 wt. %), ruthenium catalyst (0.005 mmol, 0.01 mol.%) and, whenever required, tBuOK as additive (56 mg, 0.5 mmol, 1 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars for several hours. Upon reaction completion (checked by GC) or after 24 h, autoclave was then cooled down to 25° C. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and yield was calculated based on GC purity of distilled product.

Example 3

Catalytic Hydrogenation of Aldehydes Using the Invention's Process: Influence of the R Group on the Reactivity of the Catalysts Influence of Nature of Carboxylate Ligand on Catalytic Activity in 2-methyl-4-((R)-2,2,3-trimethylcyclopent-3-en-1-yl)pent-4-enal Selective Hydrogenation

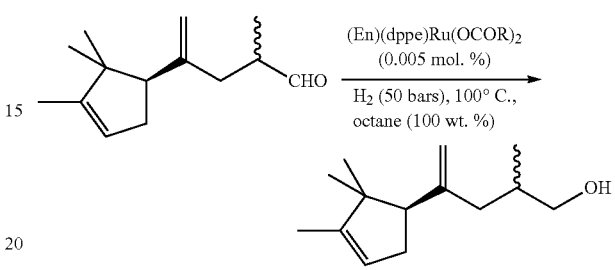

General Procedure: 2-methyl-4-((R)-2,2,3-trimethylcyclopent-3-en-1-yl)pent-4-enal (as a 40/60 (2S,4R)/(2R,4R) diastereoisomers mixture) (10.3 g, 0.05 mol), octane (10.3 g, 100 wt. %) and (ethylenediamine)[1,2-bis(diphenylphosphino)ethane]ruthenium (biscarboxylate) complex (0.0025 mmol, 0.005 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars for several hours. Upon reaction completion or after 48 h, autoclave was then cooled down to 25° C. and product purity was checked by GC analysis. It was then depressurized and purged with nitrogen (3 times 5 bars) and reaction mixture was then transferred to a round-bottomed flask and solvent was removed under vacuum. Crude product was then flash distilled in order

| Complex | Time[1] | Conv.[2] | Yield[3] | Remarks |
|---|---|---|---|---|
| * (En)(dppe)RuCl$_2$ | 24 | 0 | 0 | no tBuOK added |
| * (En)(dppe)RuCl$_2$ | 24 | 100 | 5 | 100 eq. tBuOK/Ru 95 wt. % residues |
| * (En)(dppe)RuCl$_2$ | 24 | 40 | 10 | 100 eq. tBuOK/Ru 30 wt. % residues [4] |
| * (En)(dppe)Ru(H)Cl | 24 | 0 | 0 | no tBuOK added |
| * (En)(dppe)Ru(H)Cl | 24 | 100 | 8 | 100 eq. tBuOK/Ru 92 wt. % residues |
| * (En)(dppe)Ru(H)Cl | 24 | 5 | 10 | 100 eq. tBuOK/Ru 40 wt. % residues [4] |
| * (En)(dppe)Ru(H)(HBH$_3$) | 24 | 10 | 5 | no tBuOK added |
| * (En)(dppe)Ru(H)(HBH$_3$) | 24 | 100 | 5 | 100 eq. tBuOK/Ru 95 wt. % residues |
| * (En)(dppe)Ru(H)(HBH$_3$) | 24 | 10 | 9 | no tBuOK added [4] |
| * [(En)(dppe)Ru(OAc)][BF$_4$] | 24 | 5 | 5 | no tBuOK added |
| * [(En)(dppe)Ru][BF$_4$]$_2$ | 24 | 10 | 10 | no tBuOK added |
| * (En)(dppe)Ru(OAc)$_2$ | 24 | 10 | 10 | no tBuOK added |
| * (En)(dppe)Ru(OCOC$_2$H$_5$)2 | 24 | 12 | 12 | no tBuOK added |
| * (En)(dppe)Ru(OCOCF$_3$)$_2$ | 24 | 8 | 7 | no tBuOK added |
| (En)(dppe)Ru(OCO$^t$Bu)$_2$ | 8 | 100 | 99 | no tBuOK added |
| (En)(dppe)Ru(OCOC$_6$H$_5$)$_2$ | 6 | 100 | 99 | no tBuOK added |

[1] In hours
[2] Conversion of the starting aldehyde in % (GC)
[3] Isolated yield of the primary alcohol obtained (mol. %)
[4] reaction run at 30° C.
En: ethylenediamine; dppe: 1,2-bis(diphenylphosphino)ethane.
* catalyst of the prior art and not being of formula (1)

to determine the quantity of residues formed during the reaction and isolated yield was calculated based on GC purity of distilled to product.

| Complex (R group) | Time[1] | Conv.[2] | Yield[3] | Remarks |
|---|---|---|---|---|
| * $CF_3$ | 48 | 10 | 9 | |
| * $CH_3$ | 48 | 10 | 10 | |
| * $CH_3CH_2$ | 48 | 20 | 20 | |
| $(CH_3)_2CHCH_2$ | 48 | 80 | 80 | Conv. 8 h: 40% GC |
| $(CH_3)_2CH$ | 24 | 100 | 99 | Conv. 8 h: 70% GC |
| $2,4-Cl_2C_6H_3$ | 24 | 100 | 99 | Conv. 8 h: 68% GC |
| $2,4,6-(CH_3)_3C_6H_2$ | 20 | 100 | 99 | Conv. 8 h: 74% GC |
| $4-NO_2C_6H_4$ | 18 | 100 | 99 | Conv. 8 h: 78% GC |
| 1-adamantyl | 16 | 100 | 99 | Conv. 8 h: 83% GC |
| $^tBuCH_2$ | 16 | 100 | 99 | Conv. 8 h: 85% GC |
| $^tBu$ | 10 | 100 | 99 | Conv. 8 h: 94% GC |
| Phenyl | 8 | 100 | 99 | |

[1] In hours
[2] Conversion of the starting aldehyde in % (GC)
[3] Isolated yield of the primary alcohol obtained (mol. %)
En: ethylenediamine; dppe: 1,2-bis(diphenylphosphino)ethane.
* catalyst of the prior art and not being of formula (1)

Example 4

Catalytic Hydrogenation of Aldehydes Using the Invention Process: Influence of the NN or PP Ligands on the Reactivity of the Catalysts Influence of Nature of Diphosphine Ligand

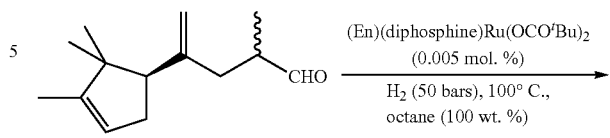

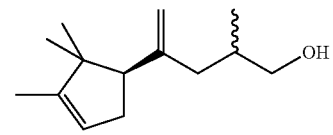

General Procedure: 2-methyl-4-((R)-2,2,3-trimethylcyclopent-3-en-1-yl)pent-4-enal (as a 40/60 (2S,4R)/(2R,4R) diastereoisomers mixture) (10.3 g, 0.05 mol), octane (10.3 g, 100 wt. %) and (ethylenediamine)(diphosphine)ruthenium (bispivalate) complex (0.0025 mmol, 0.005 mol.%) were loaded altogether in a 60 ml autoclave equipped with a mechanical stirring device. Sealed autoclave was then purged under stirring with to nitrogen (3 times 5 bars) and hydrogen (3 times 5 bars) before being pressurized to 50 bars hydrogen. It was then heated to 100° C. and hydrogen pressure was maintained to 50 bars for several hours. Upon reaction completion or after 48 h, autoclave was then cooled down to 25° C. and product purity was checked by GC analysis. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and isolated yield was calculated according to GC purity of distilled product.

| Diphosphine ligand PP | Time[1] | Conv.[2] | Yield[3] | Remarks |
|---|---|---|---|---|
| bis(diphenylphosphino)methane (dppm) | 48 | 100 | 99 | Conv. 2.5 h: 25% |
| 1,2-bis(diphenylphosphino)benzene (dppbenz) | 32 | 100 | 99 | Conv. 2.5 h: 32% |
| 1,1'-bis(diphenylphosphino)ferrocene (dppFc) | 24 | 100 | 99 | Conv. 2.5 h: 53% |
| 1,4-bis(diphenylphosphino)butane (dppb) | 20 | 100 | 99 | Conv. 2.5 h: 60% |
| 1,3-bis(diphenylphosphino)propane (dppp) | 15 | 100 | 99 | Conv. 2.5 h: 70% |
| 1,2-bis(diphenylphosphino)ethane (dppe) | 10 | 100 | 99 | Conv. 2.5 h: 75% |
| 9,9-dimethyl-4,5-bis(diphenylphosphino)xanthene (Xantphos) | 9 | 100 | 99 | Conv. 2.5 h: 85% |
| 1,2-bis(dicyclohexylphosphino)ethane (dcpe) | 2.5 | 100 | 99 | |

[1] In hours
[2] Conversion of the starting aldehyde in % (GC)
[3] Isolated yield of the primary alcohol obtained (mol. %)

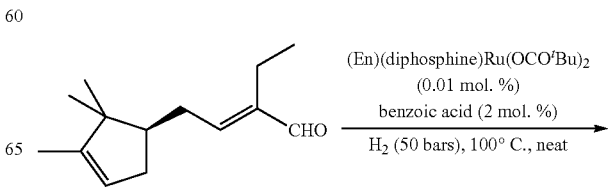

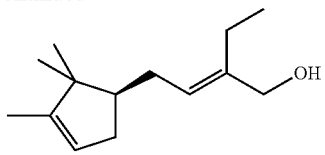

General Procedure: (R)-2-ethyl-4-(2,2,3-trimethylcyclopent-3-en-1-yl)but-2-enal (as a to 95/5 E/Z isomers mixture) (20.6 g, 0.1 mol), benzoic acid (244 mg, 1 mol.%) and (ethylenediamine)(diphosphine)ruthenium(bispivalate) complex (0.01 mmol, 0.01 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars for several minutes to several hours. Upon reaction completion, autoclave was then cooled down to 25° C. and product purity was checked by GC analysis. It was then depressurized and purged with nitrogen (3 times 5 bars). Crude product was then flash distilled in order to determine the quantity of residues formed during the reaction and isolated yield was calculated according to GC purity of distilled product.

| Diphosphine ligand PP | Time[1] | Conv.[2] | yield[3] | Selectivity[4] |
|---|---|---|---|---|
| bis(dicyclohexylphosphino)methane (dcpm) | 16 | 100 | 59.4 | 60.0 |
| 1,2-bis(diphenylphosphino)benzene (dppbz) | 12 | 100 | 82.7 | 83.5 |
| 1,2-bis(diphenylphosphino)ethane (dppe) | 6 | 100 | 89.1 | 90.0 |
| 1,4-bis(diphenylphosphino)butane (dppb) | 4 | 100 | 91.6 | 92.5 |
| bis(2-diphenylphosphinophenyl)ether (dpephos) | 9 | 100 | 94.1 | 95.0 |
| 1,1'-bis(diphenylphosphino)ferrocene (dppFc) | 2 | 100 | 95.1 | 96.0 |
| 9,9-dimethyl-4,5-bis(diphenylphosphino)xanthene (Xantphos) | 0.25 | 100 | 97.5 | 98.5 |

[1] In hours
[2] Conversion of the starting aldehyde in % (GC)
[3] Isolated yield of desired primary alcohol obtained (mol. %)
[4] 2-ethyl-4-(2,2,3-trimethylcyclopent-3-en-1-yl)butan-1-ol generally obtained as the major reaction side-product

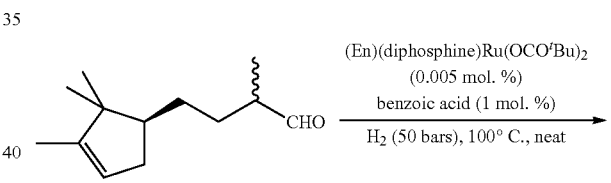

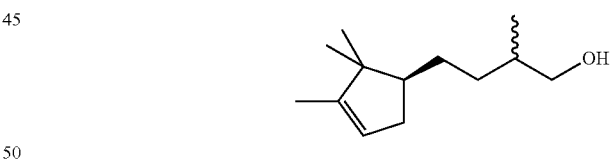

General Procedure: 2-methyl-4-((S)-2,2,3-trimethylcyclopent-3-en-1-yl)butanal (as a 50/50 diastereoisomers mixture) (19.4 g, 0.1 mol), benzoic acid (122 mg, 1 mol.%) and (ethylenediamine)(diphosphine)ruthenium(bispivalate) complex (0.005 mmol, 0.005 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars for several minutes to several hours. Upon reaction completion, autoclave was then cooled down to 25° C. and product purity was checked by GC analysis. It was then depressurized and purged with nitrogen (3 times 5 bars). Crude product was then flash distilled in order to determine the quantity of residues formed during the reaction and isolated yield was calculated according to GC purity of distilled product.

| Diphosphine ligand PP | Time[1] | Conv.[2] | yield[3] | Remark |
|---|---|---|---|---|
| (rac.)-trans-5,6-bis(diphenylphosphino)bicyclo[2.2.1]hept-2-ene ((rac.)-Norphos) | 26 | 100 | 99 | conv. 2 h: 31% |
| (rac.)-trans-1,2-bis((diphenylphosphino)methyl)Cyclobutane ((rac.)-CBD) | 18 | 100 | 99 | conv. 2 h: 46% |
| 1,2-bis(diphenylphosphino)benzene (dppbz) | 13 | 100 | 99 | conv. 2 h: 57% |
| (rac.)-2,2'-bis(diphenylphosphino)-1,1'-binaphthalene ((rac.)-Binap) | 12 | 100 | 99 | conv. 2 h: 60% |
| 1,1'-bis(diphenylphosphino)ferrocene (dppFc) | 6.5 | 100 | 99 | conv. 2 h: 83% |
| bis(2-diphenylphosphinophenyl)ether (dpephos) | 6 | 100 | 99 | conv. 2 h: 85% |
| bis(dicyclohexylphosphino)methane (dcpm) | 4 | 100 | 99 | conv. 2 h: 95% |
| 1,2-bis(diphenylphosphino)ethane (dppe) | 3 | 100 | 99 | conv. 2 h 97% |
| 9,9-dimethyl-4,5-bis(diphenylphosphino)xanthene (Xantphos) | 2 | 100 | 99 | |

[1]In hours
[2]Conversion of the starting aldehyde in % (GC)
[3]Isolated yield of desired primary alcohol obtained (mol. %)

Influence of Nature of Diamine Ligand

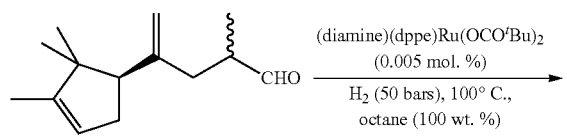

hydrogen. It was then heated to 100° C. and hydrogen pressure was maintained to 50 bars for several hours. Upon reaction completion or after 48 h, autoclave was then cooled down to 25° C. and product purity was checked by GC analysis. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and yield was then calculated based on GC purity of distilled product.

| Diamine ligand NN | Time[1] | Conv.[2] | Yield[3] | Remarks |
|---|---|---|---|---|
| N,N',dimethylethylenediamine | 48 | 80 | 80 | |
| rac. trans-1,2-diaminocyclohexane | 48 | 100 | 99 | Conv. 10 h: 50% |
| N,N-dimethylethylenediamine | 24 | 100 | 99 | Conv. 10 h: 75% |
| Pyridin-2-ylmethanamine | 16 | 100 | 99 | Conv. 10 h: 90% |
| Ethylenediamine | 10 | 100 | 99 | |

[1]In hours
[2]Conversion of the starting aldehyde in % (GC)
[3]Isolated yield of the primary alcohol obtained (mol. %)

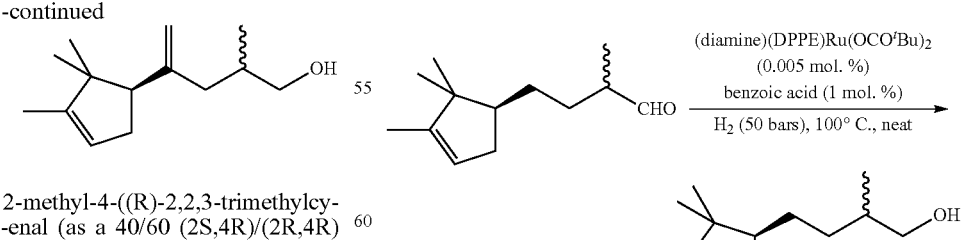

General Procedure: 2-methyl-4-((R)-2,2,3-trimethylcyclopent-3-en-1-yl)pent-4-enal (as a 40/60 (2S,4R)/(2R,4R) diastereoisomers mixture) (10.3 g, 0.05 mol), octane (10.3 g, to 100 wt. %) and (diamine)[1,2-bis(diphenylphosphino)ethane]ruthenium(bispivalate) complex (0.0025 mmol, 0.005 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars General Procedure: 2-methyl-4-((S)-2,2,3-trimethylcyclopent-3-en-1-yl)butanal (as a 50/50 diastereoisomers mixture) (19.4 g, 0.1 mol), benzoic acid (122 mg, 1 mol.%) and (diamine)[1,2-bis(diphenylphosphino)ethane]ruthenium (bispivalate) complex (0.005 mmol, 0.005 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars for several minutes to several hours. Upon reaction completion, autoclave was then cooled down to 25° C. and product purity was checked by GC analysis. It was then depressurized and purged with nitrogen (3 times 5 bars). Crude product was then flash distilled in order to determine the quantity of residues formed during the reaction and isolated yield was calculated according to GC purity of distilled product.

| Diamine ligand NN | Time[1] | Conv.[2] | yield[3] | Remark |
|---|---|---|---|---|
| Ethylenediamine | 3 | 100 | 99 | |
| N-methylethylenediamine | 3.5 | 100 | 99 | |
| N,N-dimethylethylenediamine | 4 | 100 | 99 | |
| Pyridin-2-ylmethanamine | 4 | 100 | 99 | |
| Propane-1,3-diamine | 3.5 | 100 | 99 | |
| 2,2-dimethylpropane-1,3-diamine | 3.5 | 100 | 99 | |
| Butane-1,4-diamine | 3 | 100 | 99 | |
| Piperazine | 4 | 100 | 99 | |

[1]In hours
[2]Conversion of the starting aldehyde in % (GC)
[3]Isolated yield of desired primary alcohol obtained (mol. %)

Example 5

Catalytic Hydrogenation of Aldehydes Using the Invention Process: Influence of the to Additive and In Situ Generation of the Complex (1)

Influence of Acidic Additive Sand In Situ Generation of Complex (1)

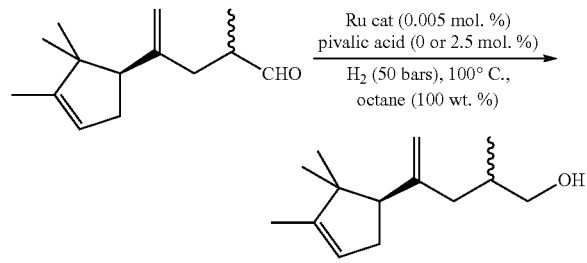

General Procedure: 2-methyl-4-((R)-2,2,3-trimethylcy-clopent-3-en-1-yl)pent-4-enal (as a 40/60 (2S,4R)/(2R,4R) diastereoisomers mixture) (10.3 g, 0.05 mol), octane (10.3 g, 100 wt. %), ruthenium catalyst (0.0025 mmol, 0.005 mol.%) and, whenever required, pivalic acid (127 mg, 1.25 mmol, 2.5 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars for several hours. Upon reaction completion (checked by GC) or after 48 h, autoclave was then cooled down to 25° C. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and isolated yield was calculated based on GC purity of distilled product.

| Ruthenium catalyst | Pivalic acid | Time[1] | Conv.[2] | Yield[3] |
|---|---|---|---|---|
| * (En)(dppe)RuCl₂ | no | 48 | 0 | 0 |
| § (En)(dppe)RuCl₂ | yes | 24 | 100 | 99 |
| * (En)(dppe)Ru(H)(BH₄) | no | 48 | 5 | 5 |
| § (En)(dppe)Ru(H)(BH₄) | yes | 15 | 100 | 99 |
| * [(En)(dppe)Ru(OAc)][BF₄] | no | 48 | 10 | 10 |
| § [(En)(dppe)Ru(OAc)][BF₄] | yes | 24 | 100 | 99 |
| * [(En)(dppe)Ru(OCOtBu)][BF₄] | no | 48 | 40 | 40 |
| § [(En)(dppe)Ru(OCOtBu)][BF₄] | yes | 20 | 100 | 99 |
| * [(En)(dppe)Ru][BF₄]₂ | no | 48 | 10 | 10 |
| § [(En)(dppe)Ru][BF₄]₂ | yes | 24 | 100 | 99 |
| * (En)(dppe)Ru(OAc)₂ | no | 48 | 10 | 9 |
| § (En)(dppe)Ru(OAc)₂ | yes | 5 | 100 | 99 |
| (En)(dppe)Ru(OCO$^t$Bu)₂ | no | 10 | 100 | 99 |
| (En)(dppe)Ru(OCO$^t$Bu)₂ | yes | 3 | 100 | 99 |

[1]In hours
[2]Conversion of the starting aldehyde in % (GC)
[3]Isolated yield of the primary alcohol obtained (mol. %)
En: ethylenediamine; dppe: 1,2-bis(diphenylphosphino)ethane.
* catalyst of the prior art and not being of formula (1)
§ catalyst of the invention being formed in situ by the addition of the pivalic acid Influence of Acidic Additives on Catalytic Activity

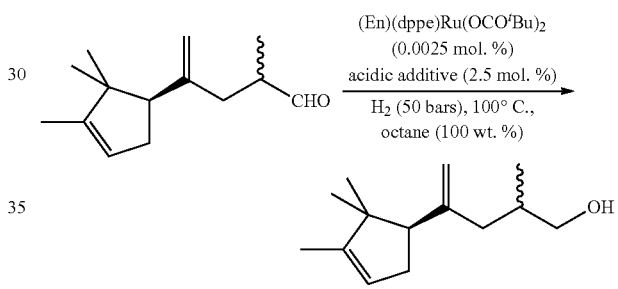

General Procedure: 2-methyl-4-((R)-2,2,3-trimethylcy-clopent-3-en-1-yl)pent-4-enal (as a 40/60 (2S,4R)/(2R,4R) diastereoisomers mixture) (10.3 g, 0.05 mol), octane (10.3 g, 100 wt. %), (ethylenediamine)[1,2-bis(diphenylphosphino)ethane]ruthenium(bispivalate) (1.9 mg, 0.0025 mmol, 0.005 mol.%) and acidic additive (1.25 mmol, 2.5 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars for several hours. Upon reaction completion (checked by GC) or after 72 h, autoclave was then cooled down to 25° C. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and isolated yield was calculated based on GC purity of distilled product.

| Acidic additive | Time[1] | Conv.[2] | Yield[3] | Remarks |
|---|---|---|---|---|
| none | 72 | 80 | 79 | |
| Hexylboronic acid | 48 | 100 | 99 | Conv. 6.5 h: 25% |

-continued

| Acidic additive | Time[1] | Conv.[2] | Yield[3] | Remarks |
|---|---|---|---|---|
| Diphenylphosphinic acid | 44 | 100 | 99 | Conv. 6.5 h: 30% |
| 2,4-dichlorobenzoic acid | 40 | 100 | 99 | Conv. 6.5 h: 40% |
| 2,4,6-trimethylbenzoic acid | 24 | 100 | 99 | Conv. 6.5 h: 65% |
| pentafluorophenol | 24 | 100 | 99 | Conv. 6.5 h: 68% |
| 4-methoxyphenol | 24 | 100 | 99 | Conv. 6.5 h: 70% |
| 4-nitrobenzoic acid | 20 | 100 | 99 | Conv. 6.5 h: 73% |
| 3,3-dimethylbutanoic acid | 20 | 100 | 98 | Conv. 6.5 h: 75% |
| 1-adamantane carboxylic acid | 20 | 100 | 99 | Conv. 6.5 h: 75% |
| 4-carbomethoxyphenol | 16 | 100 | 99 | Conv. 6.5 h: 82% |
| Pivalic acid | 12 | 100 | 99 | Conv. 6.5 h: 87% |
| 4-methoxybenzoic acid | 10 | 100 | 99 | Conv. 6.5 h: 92% |
| Benzoic acid | 8 | 100 | 99 | Conv. 6.5 h: 95% |
| 4-nitrophenol | 6.5 | 100 | 99 | |

[1]In hours
[2]Conversion of the starting aldehyde in % (GC)
[3]Isolated yield of the primary alcohol obtained (mol. %)
En: ethylenediamine; dppe: 1,2-bis(diphenylphosphino)ethane.

Despite that the amount of the catalyst in this example is half of the above examples, the additive allows to reach similar conversions and reaction time.

Example 6

Catalytic Hydrogenation of Various Aldehydes Using the Invention Process 3,6,7-Trimethyl-octa-2,6-dien-1-ol synthesis

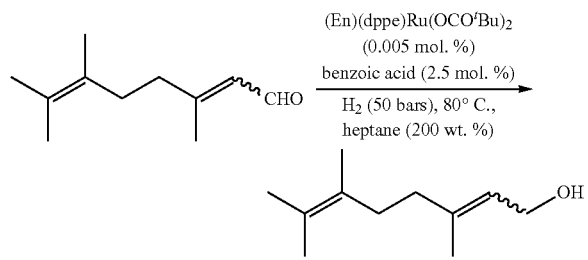

3,6,7-Trimethyl-octa-2,6-dienal (as a 40/60 Z/E isomers mixture) (166 g, 1 mol.), heptanes (332 g, 200 wt. %, technical grade), benzoic acid (3.05 g, 25 mmol, 2.5 mol.%) and to (ethylenediamine)[1,2-bis(diphenylphosphino)ethane]ruthenium(bispivalate) (38 mg, 0.05 mmol, 0.005 mol.%) were loaded altogether in a 1 l autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 80° C. and hydrogen pressure was maintained to 50 bars during all the reaction to afford desired product with 92% selectivity as a 40/60 Z/E isomers mixture. Upon reaction completion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation followed by further fractional distillation, pure 3,6,7-trimethyloct-2,6-dien-1-ol was obtained in 85% yield.

3,6,7-trimethyloct-6-en-1-ol synthesis

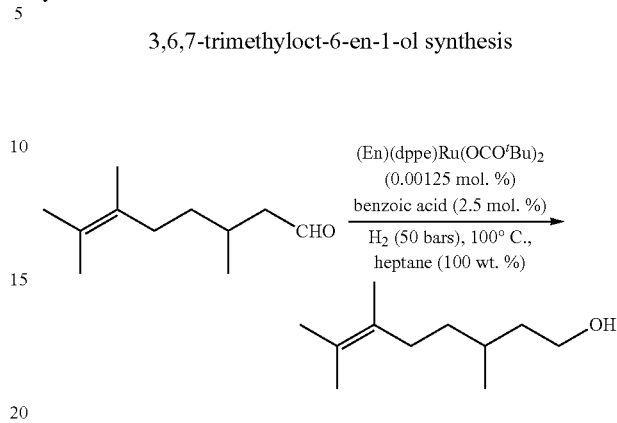

3,6,7-trimethyloct-6-enal (168 g, 1 mol.), heptane (168 g, 100 wt. %, technical grade), benzoic acid (3.05 g, 25 mmol, 2.5 mol.%) and (ethylenediamine)[1,2-bis(diphenylphosphino)ethane]ruthenium(bispivalate) (9.5 mg, 0.0125 mmol, 0.00125 mol.%) were loaded altogether in a 1 l autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with complete selectivity. Upon reaction completion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After flash distillation, pure 3,6,7-trimethyloct-6-en-1-ol was obtained in 99% yield.

3,7-dimethylocta-2,6-dien-1-ol synthesis

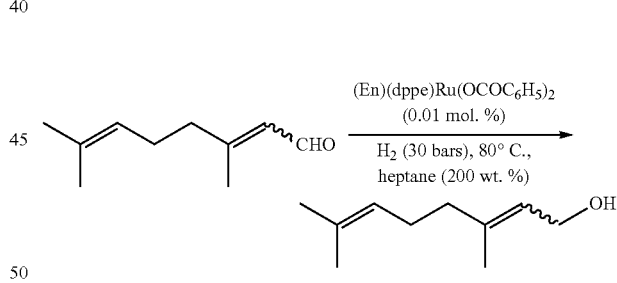

3,7-Trimethyl-octa-2,6-dienal (as a 40/60 Z/E isomers mixture) (152 g, 1 mol.), heptane (304 g, 200 wt. %, technical grade) and (ethylenediamine)[1,2-bis(diphenylphosphino)ethane]ruthenium(bisbenzoate) (80.1 mg, 0.1 mmol, 0.01 mol.%) were loaded altogether in a 1 l autoclave equipped with a mechanical stirring device. Sealed autoclave was then purged under stirring with nitrogen (3 times 5 bars) and hydrogen (3 times 5 bars) before being pressurized to 30 bars hydrogen. It was then heated to 80° C. and hydrogen pressure was maintained to 30 bars during all the reaction to afford desired product with 90% selectivity. Upon reaction completion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation followed by further fractional distillation, pure 3,7-dimethyloct-2,6-dien-1-ol was obtained in 85% yield.

3,7-dimethyloct-6-en-1-ol synthesis

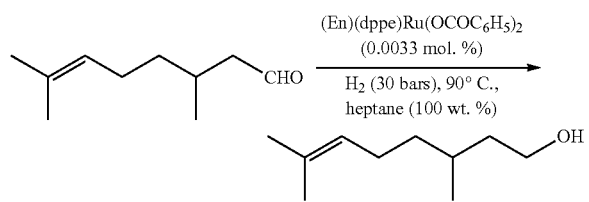

3,7-dimethyloct-6-enal (154 g, 1 mol.), heptane (154 g, 100 wt. %, technical grade) and (ethylenediamine)[1,2-bis(diphenylphosphino) ethane]ruthenium(bisbenzoate) (26.5 mg, 0.033 mmol, 0.0033 mol.%) were loaded altogether in a 1 l autoclave equipped with a mechanical stirring device. Sealed autoclave was then purged under stirring with nitrogen (3 times 5 bars) and hydrogen (3 times 5 bars) before being pressurized to 30 bars hydrogen. It was then heated to 90° C. and hydrogen pressure was maintained to 30 bars during all the reaction to afford desired product with 99% selectivity. Upon reaction completion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After flash distillation, pure 3,7-trimethyloct-6-en-1-ol was obtained in 98% yield.

3-methylhex-2-en-1-ol synthesis

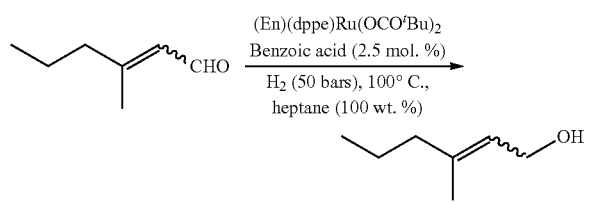

3-methylhex-2-enal (as a 40/60 Z/E isomers mixture) (112 g, 1 mol.), heptane (224 g, 100 wt. %, technical grade), benzoic acid (3.05 g, 0.025 mol., 2.5 mol.%) and (ethylenediamine) [1,2-bis(diphenylphosphino)ethane]ruthenium (bispivalate) (19 mg, 0.025 mmol, 0.0025 mol.%) were loaded altogether in a 1 l autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with 90% selectivity as a 40/60 Z/E isomers mixture. Upon reaction completion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation followed by further fractional distillation, pure 3-methylhex-2-en-1-ol was obtained in 85% yield.

3-methylhex-2-en-1-yl acetate synthesis

Aldehyde base-free chemoselective hydrogenation reaction can also efficiently be run in the presence of 1 molar equivalent of acetic anhydride in order to directly afford the acetate (via reduction of the aldehyde into the alcohol which reacts with the anhydride to provide the ester).

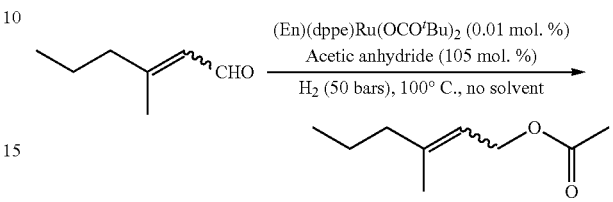

3-methylhex-2-enal (as a 40/60 Z/E isomers mixture) (112 g, 1 mol.), acetic anhydride (107 g, 1.05 mol) and (ethylenediamine)[1,2-bis(diphenylphosphino) ethane]ruthenium (bispivalate) (76 mg, 0.1 mmol, 0.01 mol.%) were loaded altogether in a 300 ml autoclave equipped with a mechanical stirring device. Sealed autoclave was then purged to under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with 96% selectivity as a 40/60 WE isomers mixture. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and concentrated under vacuum. After initial flash distillation followed by further fractional distillation, pure 3-methylhex-2-en-1-yl acetate was obtained in 90% yield.

(E)-4-methyl-5-(p-tolyl)pent-4-enal synthesis

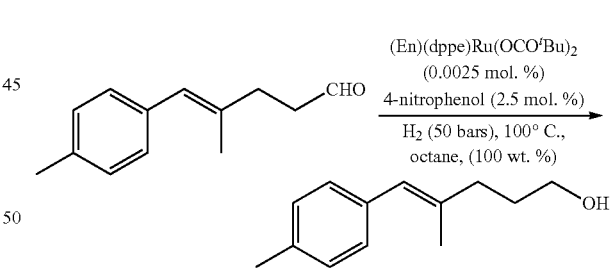

(E)-4-methyl-5-(p-tolyl)pent-4-enal (47 g, 0.25 mol.), heptane (47 g, 100 wt. %, technical grade), 4-nitrophenol (0.87 g, 6.25 mmol, 2.5 mol.%) and (ethylenediamine)[1,2-bis(diphenylphosphino)ethane]ruthenium(bispivalate) (4.8 mg, 0.00625 mmol, 0.0025 mol.%) were loaded altogether in a 300 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with complete selectivity. After complete reaction conversion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After flash distillation, (E)-4-methyl-5-(p-tolyl)pent-4-en-1-ol was obtained in 99% yield.

2,3-dimethylbut-2-en-1-ol synthesis

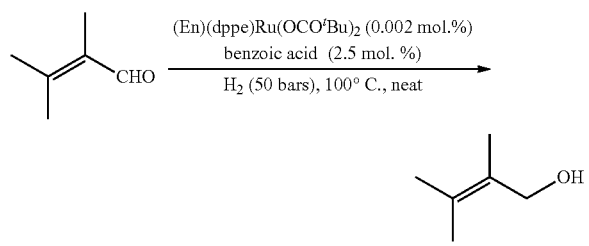

2,3-Dimethylbut-2-enal (490 g, 5 mol.), benzoic acid (15.26 g, 0.125 mol., 2.5 mol.%) and (ethylenediamine)[1,2-bis(diphenylphosphino)ethane]ruthenium(bispivalate) (76.1 mg, 0.1 mmol, 0.002 mol.%) were loaded altogether in a 1 l autoclave equipped with a mechanical stirring device. Sealed autoclave was then purged under stirring with nitrogen (3 times 5 bars) and hydrogen (3 times 5 bars) before being pressurized to 50 bars hydrogen to afford desired product with 98.5% selectivity. It was then heated to 100° C. and hydrogen pressure was maintained to 50 bars during all the reaction. After complete reaction conversion (checked by both hydrogen consumption and GC), autoclave was cooled down to 25° C. It was then depressurized and purged with nitrogen (3 times 5 bars). After flash distillation, 2,3-dimethylbut-2-en-1-ol was obtained in 98% yield.

(Z)-oct-5-en-1-ol synthesis

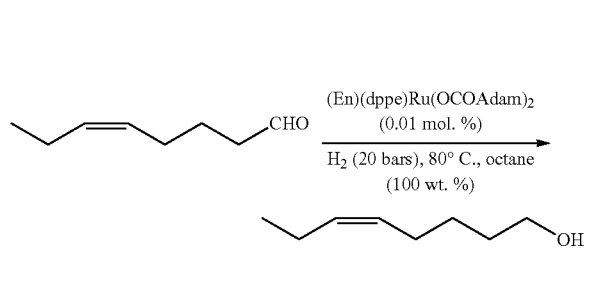

(Z)-oct-5-enal (63 g, 0.5 mol.), heptane (63 g, 100 wt. %, technical grade), and (ethylenediamine)[1,2-bis(diphenylphosphino)ethane]ruthenium[bis((adamantane-1-carboxylate)] (45.9 mg, 0.05 mmol, 0.01 mol.%) were loaded altogether in a 300 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 80° C. and hydrogen pressure was maintained to 20 bars during all the reaction to afford desired product with 95% selectivity. After complete reaction conversion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation and further fractional distillation, (Z)-oct-5-en-1-ol was obtained in 90% yield.

Undec-10-en-1-ol synthesis

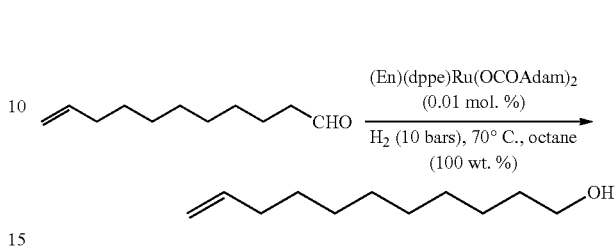

Undec-10-enal (84 g, 0.5 mol.), heptane (84 g, 100 wt. %, technical grade), and (ethylenediamine)[1,2-bis(diphenylphosphino)ethane]ruthenium[bis((adamantane-1-carboxylate)] (45.9 mg, 0.05 mmol, 0.01 mol.%) were loaded altogether in a 300 ml autoclave equipped with a mechanical stirring device. Sealed autoclave was then purged under stirring with nitrogen (3 times 5 bars) and hydrogen (3 times 5 bars) before being pressurized to 10 bars hydrogen. It was then heated to 70° C. and hydrogen pressure was maintained to 10 bars during all the reaction to afford desired product with 90% selectivity. After complete reaction conversion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation and further fractional distillation, undec-10-en-1-ol was obtained in 85% yield.

(R)-2-ethyl-4-(2,2,3-trimethylcyclopent-3-en-1-yl)but-2-en-1-ol synthesis

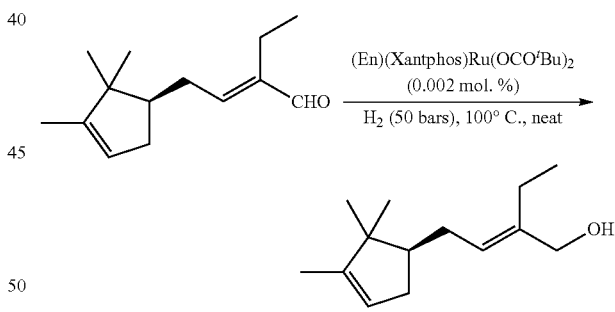

(R)-2-ethyl-4-(2,2,3-trimethylcyclopent-3-en-1-yl)but-2-enal (as a 95/5 E/Z isomers mixture) (412 g, 2 mol.), benzoic acid (2.44 g, 0.02 mol., 1 mol.%) and (ethylenediamine)[9,9-dimethyl-4,5-bis(diphenylphosphino)xanthene]ruthenium (bispivalate) (37.6 mg, 0.04 mmol, 0.002 mol.%) were loaded altogether in a 1 L autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with 98.5% selectivity as a 95/5 E/Z isomers mixture and no loss of optical purity. Upon complete reaction conversion (checked by both hydrogen consumption and GC), autoclave was cooled down to 25° C. It was then depressurized and

(R)-2-methyl-4-(2,2,3-trimethylcyclopent-3-en-1-yl) but-2-en-1-ol synthesis

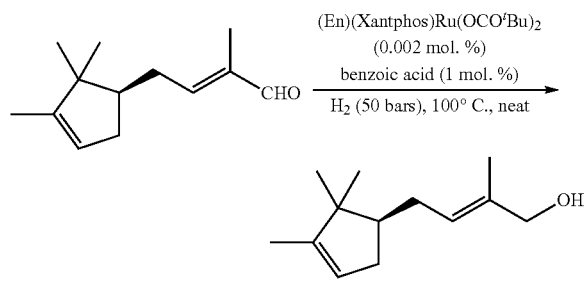

(R)-2-methyl-4-(2,2,3-trimethylcyclopent-3-en-1-yl)but-2-enal (as a 98/2 E/Z isomers mixture) (384 g, 2 mol.), benzoic acid (2.44 g, 0.02 mol., 1 mol.%) and (ethylenediamine) [9,9-dimethyl-4,5-bis(diphenylphosphino)xanthene] ruthenium(bispivalate) (37.6 mg, 0.04 mmol, 0.002 mol.%) were loaded altogether in a 1 L autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with 97.5% selectivity as a 98/2 E/Z isomers mixture and no loss of optical purity. Upon complete reaction conversion (checked by both hydrogen consumption and GC), autoclave was cooled down to 25° C. It was then depressurized and purged with nitrogen (3 times 5 bars). After flash distillation, (R)-2-methyl-4-(2,2,3-trimethylcyclopent-3-en-1-yl)but-2-en-1-ol was obtained in 96.5% yield.

2-methyl-4-((S)-2,2,3-trimethylcyclopent-3-en-1-yl) butan-1-ol synthesis

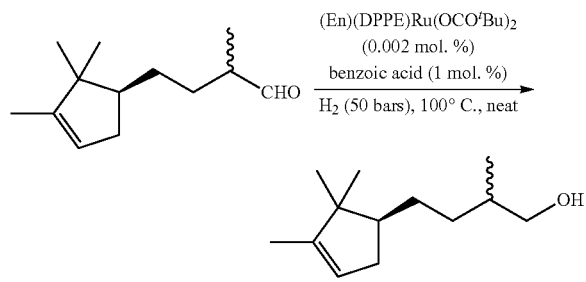

2-methyl-4-((S)-2,2,3-trimethylcyclopent-3-en-1-yl)butanal (as a 50/50 diastereoisomers mixture) (388 g, 2 mol.), benzoic acid (2.44 g, 0.02 mol., 1 mol.%) and (ethylenediamine) [1,2-bis(diphenylphosphino)ethane]ruthenium (bispivalate) (30.5 mg, 0.04 mmol, 0.002 mol.%) were loaded altogether in a 1 L autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with more than 99.0% selectivity as a 50/50 diastereoisomers mixture and no loss of optical purity. Upon complete reaction conversion (checked by both hydrogen consumption and GC), autoclave was cooled down to 25° C. It was then depressurized and purged with nitrogen (3 times 5 bars). After flash distillation, 2-methyl-4-((S)-2,2,3-trimethylcyclopent-3-en-1-yl)butan-1-ol was obtained in more than 98.0% yield.

hexa-2,4-dien-1-yl pivalate synthesis

In the case of hexa-2,4-dienal, if aldehyde base-free chemoselective hydrogenation reaction generally afforded desired product in much better yields compared to classical systems due to really high starting material sensitivity to basic conditions, catalytic activity was then noticeably increased running the reaction in the presence of 1 molar equivalent of various carboxylic acid anhydrides in order to afford hexa-2,4-dien-1-ol esters via reduction of the aldehyde into the alcohol which reacts with anhydride used to provide the corresponding ester.

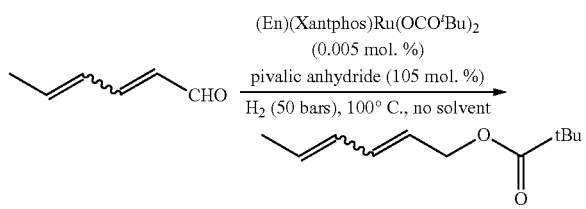

Hexa-2,4-dienal (as a 85/15 (E,E)/(Z,E) isomers mixture) (192 g, 2 mol.), pivalic anhydride (391 g, 2.1 mol.) and (ethylenediamine)[9,9-dimethyl-4,5-bis(diphenylphosphino) xanthene]ruthenium(bispivalate) (94.2 mg, 0.1 mmol, 0.005 mol.%) were loaded altogether in a 1 L autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with 95% selectivity as a 85/15 (E,E)/(Z,E) isomers mixture. Upon reaction completion (checked by both hydrogen consumption and GC), autoclave was then cooled down to 25° C. It was then depressurized and purged with nitrogen (3 times 5 bars). After initial flash distillation followed by further fractional distillation, pure hexa-2,4-dien-1-yl pivalate was obtained in 90% yield.

hexa-2,4-dien-1-ol esters synthesis

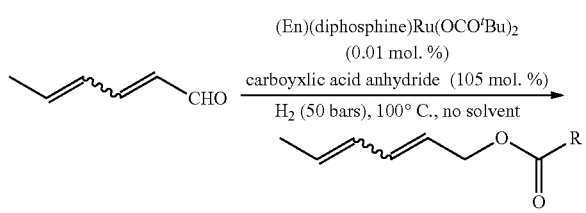

General Procedure: Hexa-2,4-dienal (as a 85/15 (E,E)/(Z,E) isomers mixture) (9.6 g, 0.1 mol.), carboxylic acid anhydride (0.105 mol.) and (ethylenediamine)(diphosphine)

ruthenium(bispivalate) (0.01 mmol, 0.01 mol.%) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product. Upon reaction completion (checked by both hydrogen consumption and GC), autoclave was then cooled down to 25° C.

It was then depressurized and purged with nitrogen (3 times 5 bars) and reaction mixture was then transferred to a round-bottomed flask. It was diluted with diethylether and washed with a saturated sodium hydrogencarbonate aqueous solution for carboxylic acid removal and then with water. After drying over magnesium sulfate and solvent removal, crude product was flash distilled in order to determine the quantity of residues formed during the reaction and isolated yield was calculated according to GC purity of distilled product.

| anhydride used product | Diphosphine ligand PP | T.[1] | Conv.[2] | Yield[3] | Select.[4] |
|---|---|---|---|---|---|
| Pivalic Anhydride 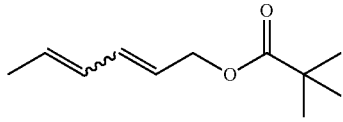 | 9,9-dimethyl-4,5-bis(diphenylphosphino)xanthene (Xantphos) | 3 | 100 | 93.1 | 95.0 |
| Pivalic Anhydride [5] 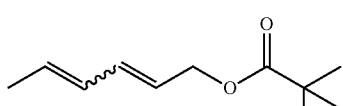 | 9,9-dimethyl-4,5-bis(diphenylphosphino)xanthene (Xantphos) | 3.5 | 100 | 92.5 | 94.5 |
| Pivalic Anhydride 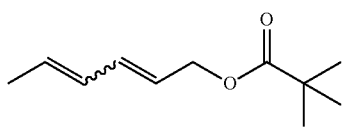 | 1,2-bis(diphenylphosphino)ethane (dppe) | 6 | 100 | 88.2 | 90.0 |
| Isobutyric anhydride 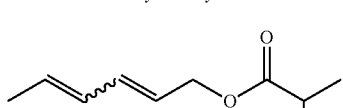 | 1,2-bis(diphenylphosphino)ethane (dppe)) | 5 | 100 | 83.7 | 85.0 |
| Benzoic anhydride [6] 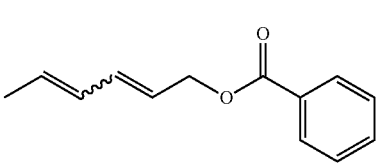 | 1,2-bis(diphenylphosphino)ethane (dppe) | 5 | 100 | 79.5 | 82 |
| Butyric anhydride 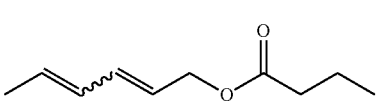 | 1,2-bis(diphenylphosphino)ethane (dppe) | 7 | 100 | 78.0 | 80 |
| Proprionic anhydride 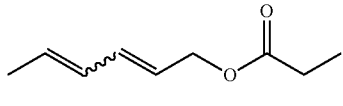 | 1,2-bis(diphenylphosphino)ethane (dppe) | 7 | 100 | 76.5 | 78.5 |

| anhydride used product | Diphosphine ligand PP | T.[1] | Conv.[2] | Yield[3] | Select.[4] |
|---|---|---|---|---|---|
| Acetic anhydride 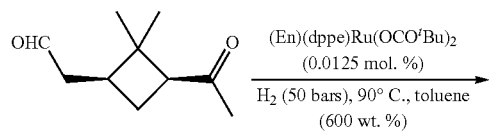 | 1,2-bis(diphenylphosphino)ethane (dppe) | 8 | 100 | 76.0 | 78.0 |

[1] In hours
[2] Conversion of the starting aldehyde in % (GC)
[3] Isolated yield of desired ester obtained (mol. %)
[4] Pivalic anhydride was dosed under pressure using a Lewa ®-type pump following hydrogen consumption and with nearly no accumulation observed.
[5] Reaction was run in the presence of 100 wt. % toluene respect to starting material due to solubility issues

Example 7

Catalytic Hydrogenation of Various Aldehydes Using the Invention's Process: Chemoselectivity 1-((1S,3R)-3-(2-hydroxyethyl)-2,2-dimethylcyclopropyl)propan-2-one synthesis

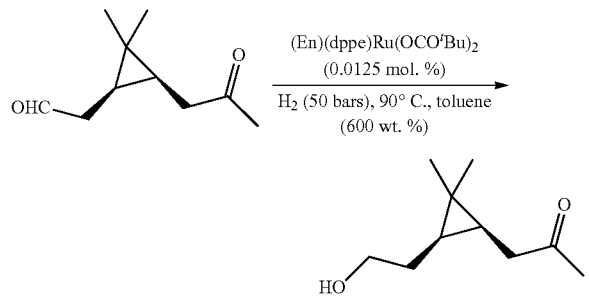

2-((1R,3S)-2,2-dimethyl-3-(2-oxopropyl)cyclopropyl)acetaldehyde (8.4 g, 0.05 mol.), to toluene (50 g, 600 wt. %) and (ethylenediamine)[1,2-bis(diphenylphosphino)ethane]ruthenium(bispivalate) (4.8 mg, 0.00625 mmol, 0.0125 mol.%) were loaded altogether in a 125 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 90° C. and hydrogen pressure was maintained to 50 bars during all the reaction to afford desired product with 95% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, 1-((1S,3R)-3-(2-hydroxyethyl)-2,2-dimethylcyclopropyl)propan-2-one was obtained in 90% yield.

1-((1S,3S)-3-(2-hydroxyethyl)-2,2-dimethylcyclobutyl)ethanone synthesis

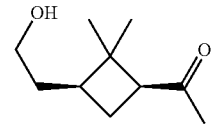

2-((1S,3S)-3-acetyl-2,2-dimethylcyclobutyl)acetaldehyde (8.4 g, 0.05 mol.), toluene (50 g, 600 wt. %) and (ethylenediamine)[1,2-bis(diphenylphosphino)ethane]ruthenium (bispivalate) (4.8 mg, 0.00625 mmol, 0.0125 mol.%) were loaded altogether in a 125 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 90° C. and hydrogen pressure was maintained to 50 bars during all the reaction to afford desired product with 98% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, 1-((1S,3S)-3-(2-hydroxyethyl)-2,2-dimethylcyclobutyl)ethanone was obtained in 94% yield.

4-((1R,2S)-2-(hydroxymethyl)-3,3-dimethyl-7-methylenecycloheptyl)butan-2-one synthesis

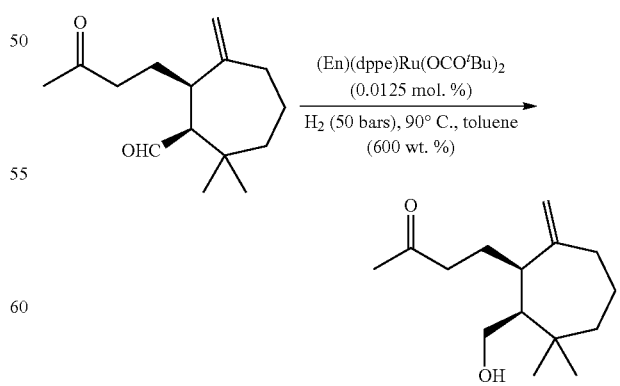

(1S,7R)-2,2-dimethyl-6-methylene-7-(3-oxobutyl)cycloheptanecarbaldehyde (11.8 g, 0.05 mol.), toluene (70.8 g, 600 wt. %) and (ethylenediamine)[1,2-bis(diphenylphosphino)

ethane]ruthenium(bispivalate) (4.8 mg, 0.00625 mmol, 0.0125 mol.%) were loaded altogether in a 200 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 90° C. and hydrogen pressure was maintained to 30 bars during all the reaction to afford desired product with 92% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, 4-((1R,2S)-2-(hydroxymethyl)-3,3-dimethyl-7-methylenecycloheptyl) butan-2-one was obtained in 85% yield.

4-((1R,4S)-4-(5-hydroxypent-1-en-2-yl)-2,2-dimethylcyclobutyl)butan-2-one synthesis

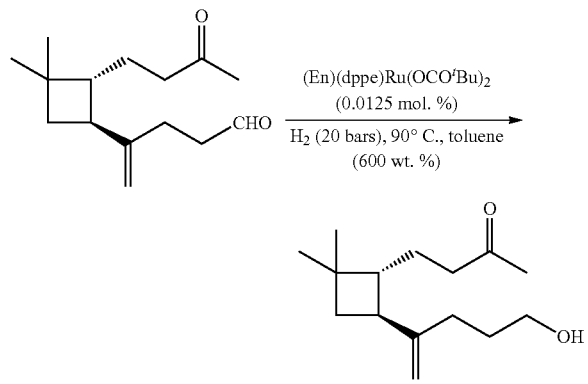

4-((1S,2R)-3,3-dimethyl-2-(3-oxobutyl)cyclobutyl)pent-4-enal (11.8 g, 0.05 mol.), toluene (70.8 g, 600 wt. %) and (ethylenediamine) [1,2-bis(diphenylphosphino) ethane]ruthenium(bispivalate) (4.8 mg, 0.00625 mmol, 0.0125 mol.%) were loaded altogether in a 200 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was maintained to 20 bars during all the reaction to afford desired product with 95% selectivity. Upon reaction completion (checked by both hydrogen consumption and GC), to autoclave was then cooled down to 25° C. It was then depressurized and purged with nitrogen (3 times 5 bars) and reaction mixture was then transferred to a round-bottomed flask and solvent was removed under vacuum. After flash chromatography, 4-((1R,4S)-4-(5-hydroxypent-1-en-2-yl)-2,2-dimethylcyclobutyl)butan-2-one was obtained in 90% yield.

Racemic endo 1-(3-(2-hydroxyethyl)bicyclo[2.2.1]heptan-2-yl)propan-2-one synthesis

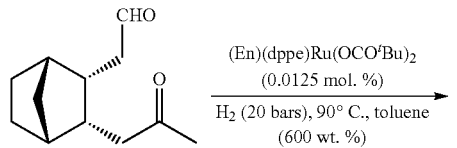

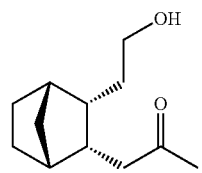

Racemic endo 2-(3-(2-oxopropyl)bicyclo[2.2.1]heptan-2-yl)acetaldehyde (9.7 g, 0.05 mol.), toluene (58 g, 600 wt. %) and (ethylenediamine) [1,2-bis(diphenylphosphino)ethane]ruthenium(bispivalate) (4.8 mg, 0.00625 mmol, 0.0125 mol.%) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was maintained to 50 bars during all the reaction to afford desired product with 97% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, racemic endo 1-(3-(2-hydroxyethyl) bicyclo[2.2.1]heptan-2-yl)propan-2-one was obtained in 92% yield.

7-hydroxyheptan-2-one synthesis

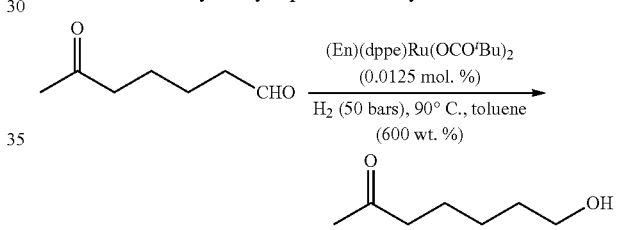

6-oxoheptanal (12.8 g, 0.1 mol.), toluene (76.8 g, 600 wt. %) and (ethylenediamine)[1,2-bis(diphenylphosphino) ethane]ruthenium (bispivalate) (9.6 mg, 0.0125 mmol, 0.0125 mol.%) were loaded altogether in a 200 ml autoclave equipped with a mechanical stirring device. Sealed autoclave was then purged under stirring with nitrogen (3 times to 5 bars) and hydrogen (3 times 5 bars) before being pressurized to 20 bars hydrogen. It was then heated to 90° C. and hydrogen pressure was maintained to 50 bars during all the reaction to afford desired product with 94% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, 7-hydroxyheptan-2-one was obtained in 90% yield.

1-(5,5-dimethylcyclohex-1-en-1-yl)-6-hydroxyhexan-1-one synthesis

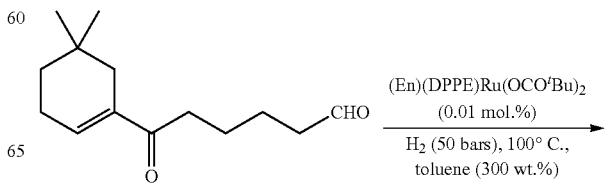

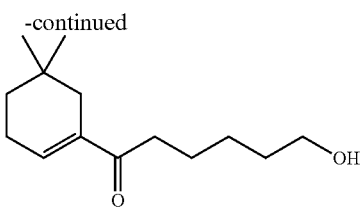

6-(5,5-dimethylcyclohex-1-en-1-yl)-6-oxohexanal (6.67 g, 0.03 mol.), toluene (20 g, 300 wt. %) and (ethylenediamine)[1,2-bis(diphenylphosphino)ethane]ruthenium (bispivalate) (2.3 mg, 0.003 mmol, 0.01 mol.%) were loaded altogether in a 125 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with 97.5% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, 1-(5,5-dimethylcyclohex-1-en-1-yl)-6-hydroxyhexan-1-one was obtained in 93% yield.

1-(5,5-dimethylcyclohex-1-en-1-yl)-5-hydroxy-4-methylpentan-1-one synthesis

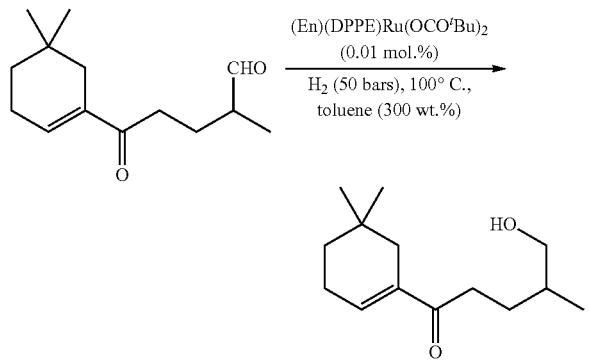

5-(5,5-dimethylcyclohex-1-en-1-yl)-2-methyl-5-oxopentanal (6.67 g, 0.03 mol.), toluene (20 g, 300 wt. %) and (ethylenediamine)[1,2-bis(diphenylphosphino)ethane]ruthenium (bispivalate) (2.3 mg, 0.003 mmol, 0.01 mol.%) were loaded altogether in a 125 ml autoclave equipped with a mechanical stirring device. Sealed autoclave was then purged to under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction to afford desired product with 90.0% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, 1-(5,5-dimethylcyclohex-1-en-1-yl)-5-hydroxy-4-methylpentan-1-one was obtained in 85% yield.

Catalytic Hydrogenation of Various Aldehydes Using the Invention's Process: Chemoselectivity in Aldehyde Versus Ketone Competitive Experiments

2-methyl-4-((R)-2,2,3-trimethylcyclopent-3-en-1-yl)pent-4-enal versus (R,E)-3,3-dimethyl-5-(2,2,3-trimethylcyclopent-3-en-1-yl)pent-4-en-2-one

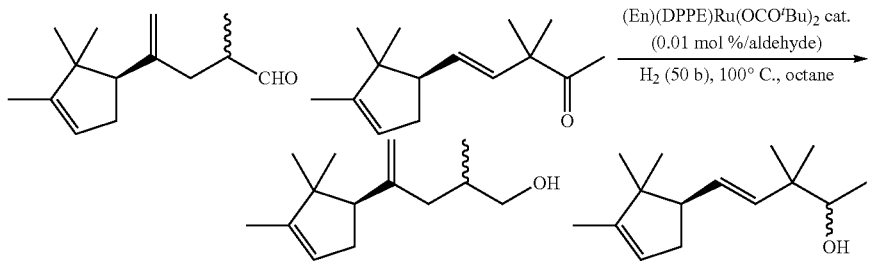

2-methyl-4-((R)-2,2,3-trimethylcyclopent-3-en-1-yl)pent-4-enal (as a 40/60 (2S,4R)/(2R,4R) diastereoisomers mixture) (10.3 g, 0.05 mol), (R,E)-3,3-dimethyl-5-(2,2,3-trimethylcyclopent-3-en-1-yl)pent-4-en-2-one (11.0 g, 0.05 mol.), octane (21.3 g, 100 wt. %) and (ethylenediamine)[1,2-bis(diphenylphosphino)ethane]ruthenium (bispivalate) complex (3.8 mg, 0.005 mmol., 0.01 mol.%/aldehyde) were loaded altogether were loaded altogether in a 100 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction that was followed by GC analysis.

| t (h) | 0 | 0.5 | 1 | 1.5 | 2 | 2.5 | 3 |
|---|---|---|---|---|---|---|---|
| Aldehyde GC % conversion | 0 | 60.1 | 82.9 | 91.0 | 96.4 | 99.1 | 100 |
| Ketone GC % conversion | 0 | 0.0 | 0.05 | 0.10 | 0.15 | 0.20 | 0.25 |
| primary vs. secondary Alcohol formation selectivity | | 100 | 99.9 | 99.8 | 99.7 | 99.6 | 99.5 |

Note:

primary vs. secondary alcohol selectivity (%) = 100 × (% primary alcohol − % secondary alcohol)/(% primary alcohol + % secondary alcohol)

2-methyl-4-((R)-2,2,3-trimethylcyclopent-3-en-1-yl) pent-4-enal versus trans 1-(2,2,6-trimethylcyclohexyl)hexan-3-one

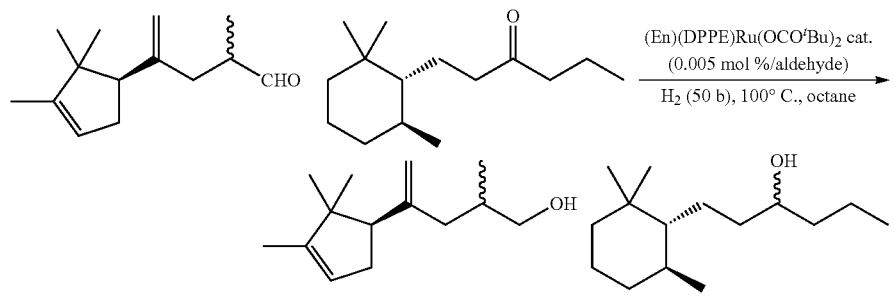

2-methyl-4-((R)-2,2,3-trimethylcyclopent-3-en-1-yl) pent-4-enal (as a 40/60 (2S,4R)/(2R,4R) diastereoisomers mixture) (10.3 g, 0.05 mol), racemic trans 1-(2,2,6-trimethylcyclohexyl)hexan-3-one (11.2 g, 0.05 mol.), octane (21.5 g, 100 wt. %) and (ethylenediamine)[1,2-bis(diphenylphosphino)ethane]ruthenium(bispivalate) complex (1.9 mg, 0.0025 mmol, 0.005 mol.%/aldehyde) were loaded altogether were loaded altogether in a 100 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction that was followed by GC analysis.

| t (h) | 0 | 0.5 | 1 | 2 | 3 | 4 | 6 | 7 | 9 |
|---|---|---|---|---|---|---|---|---|---|
| Aldehyde GC % conversion | 0 | 34.2 | 51.5 | 69.1 | 83.4 | 89.2 | 95.9 | 98.2 | 100 |
| Ketone GC % conversion | 0 | 0.1 | 0.2 | 0.4 | 0.6 | 0.8 | 1.2 | 1.4 | 1.8 |
| Primary vs. secondary Alcohol formation selectivity (%) | | 99.4 | 99.2 | 98.8 | 98.6 | 98.2 | 97.5 | 97.2 | 96.5 |

Note:
primary vs. secondary alcohol selectivity (%) = 100 × (% primary alcohol – % secondary alcohol)/(% primary alcohol + % secondary alcohol)

FIG. 1b: graph corresponding to the above table.

2-methyl-4-((R)-2,2,3-trimethylcyclopent-3-en-1-yl) pent-4-enal versus acetophenone

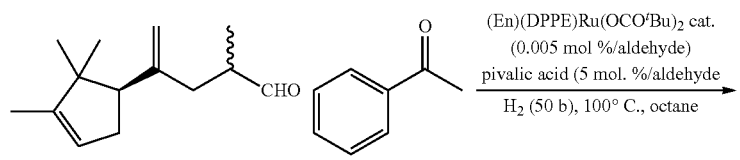

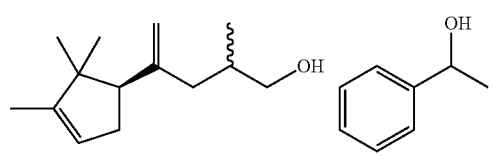

2-methyl-4-((R)-2,2,3-trimethylcyclopent-3-en-1-yl) pent-4-enal (as a 40/60 (2S,4R)/(2R,4R) diastereoisomers mixture) (10.3 g, 0.05 mol), acetophenone (6.0 g, 0.05 mol.), octane (48.9 g, 300 wt. %), pivalic acid (0.254 g, 2.5 mmol, 5 mol.%/aldehyde) and (ethylenediamine) [1,2-bis(diphenylphosphino)ethane]ruthenium(bispivalate) complex (1.9 mg, 0.0025 mmol., 0.005 mol.%/aldehyde) were loaded altogether were loaded altogether in a 100 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars during all the reaction that was followed by GC analysis.

| t (h) | 0 | 0.25 | 0.5 | 1 | 1.5 | 2 | 3 | 4 | 5 |
|---|---|---|---|---|---|---|---|---|---|
| Aldehyde GC % conversion | 0 | 25 | 40 | 65 | 80 | 87 | 95 | 99 | 100 |
| Ketone GC % conversion | 0 | 0.15 | 0.3 | 0.6 | 0.9 | 1.2 | 1.8 | 2.4 | 3.1 |
| primary vs. secondary Alcohol formation selectivity (%) | | 98.8 | 98.5 | 98.2 | 97.8 | 97.3 | 96.3 | 95.3 | 94.0 |

Note:
primary vs. secondary alcohol selectivity (%) = 100 × (% primary alcohol − % secondary alcohol)/(% primary alcohol + % secondary alcohol)

FIG. 2: graph corresponding to the above table.

What is claimed is:

1. A process for the reduction by hydrogenation, using molecular $H_2$, of a $C_5$-$C_{20}$ substrate of formula

(I)

wherein $R^a$ represents a $C_4$-$C_{19}$ linear, branched or cyclic alkyl, alkenyl or alkadienyl group optionally comprising an aromatic ring and optionally comprising one, two or three functional groups selected among ketone, ether, carbon-carbon double or triple bond and carboxylic groups; into the corresponding alcohol or diol, wherein said process is carried out in the presence of at least one catalyst or pre-catalyst of formula

[Ru(PP)(NN)(RCOO)$_2$]  (1)

wherein NN represents a $C_2$-$C_{20}$ bidentate ligand of formula

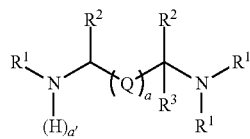
(B)

wherein a and a', simultaneously or independently, represent 0 or 1 (when a' is 0 then the nitrogen atom is part of an aromatic heterocycle);

the $R^1$, taken separately, represent, simultaneously or independently, a hydrogen atom or a $C_{1-6}$ linear, branched or cyclic alkyl group or a benzyl group optionally substituted; two $R^1$, taken together, may form a saturated heterocycle containing 5 to 7 atoms and including the atoms to which said $R^1$ are bonded, said heterocycle being optionally substituted;

$R^2$ and $R^3$, taken separately, represent, simultaneously or independently, a hydrogen atom, a $C_{1-6}$ linear, branched alkyl group or a $C_{6-10}$ aromatic group optionally substituted; a $R^1$ and an adjacent $R^2$, taken together, may form a saturated or aromatic heterocycle containing 5 to 8 atoms and including the atoms to which said $R^1$ and $R^2$ are bonded, and optionally containing one additional nitrogen or oxygen atom; two $R^2$, taken together, may form a saturated or unsaturated ring having 5 to 8 atoms and including the carbon atoms to which said $R^2$ or $R^3$ groups are bonded, said ring optionally containing one additional nitrogen and/or oxygen atom; and Q represents a group of formula

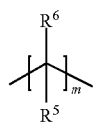
(i)

wherein m is 1 or 2, and $R^5$ and $R^6$ represent, simultaneously or independently, a hydrogen atom, a $C_{1-6}$ linear, branched or cyclic alkyl or, a $C_{6-10}$ aromatic group optionally substituted; two distinct $R^6$ and/or $R^5$ groups, taken together, may form a $C_{3-8}$ saturated ring optionally substituted, including the atoms to which said $R^6$ and/or $R^5$, groups are bonded, and optionally containing one or two additional nitrogen or oxygen atoms;

the optional substituents of $R^1$, $R^2$, $R^3$, $R^5$, $R^6$ being one, two, three or four groups selected amongst i) halogens (in particular when said substituents are on aromatic moieties) iii) $C_{1-6}$ alkoxy, alkyl, alkenyl, or iv) a benzyl group or a fused or non-fused phenyl group, said group being optionally substituted by one, two or three halogen, $C_{1-8}$ alkyl, alkoxy, amino, nitro, ester, sulfonate or halo- or perhalo-hydrocarbon groups;

PP represents a $C_6$-$C_{50}$ bidentate ligand of formula

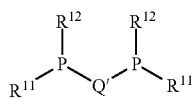
(C)

wherein $R^{11}$ and $R^{12}$, when taken separately, represent, simultaneously or independently, a $C_{3-6}$ branched or cyclic alkyl group or a $C_{6-10}$ aromatic group optionally substituted; and Q' represents a group of formula

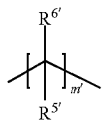

(i')

wherein m' is 1, 2, 3 or 4 and $R^{5'}$ and $R^{6'}$ represent, simultaneously or independently, a hydrogen atom, a $C_{1-6}$ linear or branched alkyl group or a $C_{6-10}$ aromatic group optionally substituted; two distinct $R^{6'}$ and/or $R^{5'}$ groups, taken together, may form a $C_3$ to $C_8$ saturated or unsaturated ring optionally substituted, including the atoms to which said $R^{6'}$ and/or $R^{5'}$ groups are bonded, and optionally containing one or two additional nitrogen or oxygen atoms; or a $C_{10}$-$C_{16}$ metallocenediyl, a 2,2'-diphenyl, a 1,1'-binaphthalene-2,2'-diyl, a benzenediyl, a naphthalenediyl, 2,3-bicyclo[2:2:1]hept-5-enediyl, 4,6-phenoxazinediyl, 4,5-(9,9-dimethyl)-xanthenediyl, or bis(phen-2-yl)ether group optionally substituted;

the optional substituents of $R^{5'}$, $R^{6'}$, $R^{11}$ and $R^{12}$ are one to five halogens (in particular when said substituents are on aromatic moieties), or one, two or three i) $C_{1-6}$ linear or branched alkyl alkoxy, groups or halo- or perhalo-hydrocarbon, amine groups, ii) $COOR^h$ wherein $R^h$ is a $C_{1-6}$ linear, branched or cyclic alkyl group, iii) $NO_2$ group, or iv) a benzyl group or a fused or non-fused phenyl group, said group being optionally substituted by one, two or three halogen, $C_{1-8}$ alkyl, alkoxy, amino, nitro, ester, sulfonate or halo- or perhalo-hydrocarbon groups; and each R represents, simultaneously or independently, a $C_2$-$C_{12}$ hydrocarbon group branched or cyclic in the α and/or β position, and said hydrocarbon group is optionally comprising one to five heteroatom selected amongst halogen, oxygen and nitrogen atoms; and optionally of an acidic additive.

2. The process according to claim 1, wherein each R represents, simultaneously or independently:

a $C_{2-12}$ alkyl group branched or cyclic in the α and/or β position optionally substituted by one phenyl group optionally substituted by one to five halogen atoms and/or by $C_{1-4}$ alkyl or alkoxyl groups; and optionally comprising one OH, amino or ether functional group; or a phenyl group optionally substituted by one to three, or five, halogen atoms and/or by $C_{1-4}$ alkyl or alkoxyl groups and/or by nitro groups.

3. The process according to claim 1, wherein the bidentate NN ligand is a compound of formula

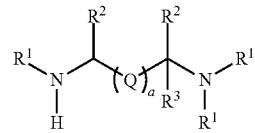

(B')

wherein a represents 0 or 1;

each $R^1$, simultaneously or independently, represents a hydrogen atom or a $C_{1-4}$ linear or branched alkyl group or a benzyl group optionally substituted;

$R^2$ and $R^3$, taken separately, represent, simultaneously or independently, a hydrogen atom, a $C_{1-4}$ linear or branched alkyl group optionally substituted or a phenyl group optionally substituted; a $R^1$ and an adjacent $R^2$, taken together, may form a saturated heterocycle containing 6 atoms and including the atoms to which said $R^1$ and $R^2$ are bonded, and being optionally substituted; two $R^2$ taken together, may form a saturated ring having 5 to 6 atoms and including the carbon atoms to which said $R^2$ groups are bonded; and Q represents a group of formula

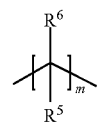

(i)

wherein m is 1 or 2, and $R^5$ and $R^6$ represent, simultaneously or independently, a hydrogen atom, a $C_{1-4}$ linear or branched alkyl group or a phenyl group optionally substituted.

4. The process according to claim 1, wherein said ligand NN is represented by formula

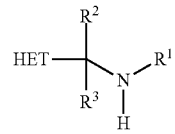

(B'')

wherein $R^1$ represents a hydrogen atom or a $C_{1-4}$ linear or branched alkyl group;

$R^2$ and $R^3$, taken separately, represent, simultaneously or independently, a hydrogen atom, a $C_{1-4}$ linear or branched alkyl group; and HET represents a 2-pyridinyl group optionally substituted by one, two or three $C_{1-4}$ linear or branched alkyl groups or by a benzyl group or a fused or non-fused phenyl or indanyl group, said group being optionally substituted by one, two or three halogen, $C_{1-4}$ alkyl, alkoxy, amino, nitro, ester or sulfonate groups, such as a 2-pyridyl, 2-quinolinyl or a methyl-2-pyridinyl.

5. The process according to claim 1, wherein each $R^{11}$ and $R^{12}$ represent each, simultaneously or independently, a $C_{4-6}$ branched or cyclic alkyl group or a phenyl group optionally substituted.

6. The process according to claim 1, wherein said PP ligand is a compound of formula (C) wherein $R^{11}$ and $R^{12}$ represent, simultaneously or independently, a $C_{4-6}$ branched or cyclic alkyl group or a phenyl group optionally substituted; and Q' represents a $C_1$-$C_4$ alkanediyl radical optionally substituted, a $C_{10}$-$C_{12}$ ferrocenediyl, a 2,2'-diphenyl, a 1,2-benzenediyl or a naphthalenediyl group.

7. The process according to claim 1, wherein said acidic additive may be selected amongst the weak protic acids having a $pK_a$ comprised between 2 and 11.

8. The process according to claim 1, wherein the acidic additive is selected amongst:
a carboxylic acid of formula RCOOH, wherein R is as defined above in formula (1); and
phenol ($C_6H_5OH$) and a phenol substituted by one or two, or up to five, halogen atoms and/or $C_{1-4}$ alkyl or alkoxyl groups and/or nitro groups and/or carboalkoxy groups.

9. A ruthenium complex of formula

[Ru(PP)(NN)(RCOO)$_2$]  (1)

wherein NN represents a $C_2$-$C_{20}$ bidentate ligand of formula

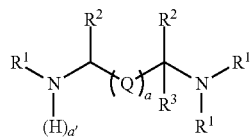

(B)

wherein a and a', simultaneously or independently, represent 0 or 1 (when a' is 0 then the nitrogen atom is part of an aromatic heterocycle);
the $R^1$, taken separately, represent, simultaneously or independently, a hydrogen atom or a $C_{1-6}$ linear, branched or cyclic alkyl group or a benzyl group optionally substituted; two $R^1$, taken together, may form a saturated heterocycle containing 5 to 7 atoms and including the atoms to which said $R^1$ are bonded, said heterocycle being optionally substituted;
$R^2$ and $R^3$, taken separately, represent, simultaneously or independently, a hydrogen atom, a $C_{1-6}$ linear, branched alkyl group or a $C_{6-10}$ aromatic group optionally substituted; a $R^1$ and an adjacent $R^2$, taken together, may form a saturated or aromatic heterocycle containing 5 to 8 atoms and including the atoms to which said $R^1$ and $R^2$ are bonded, and optionally containing one additional nitrogen or oxygen atom; two $R^2$, taken together, may form a saturated or unsaturated ring having 5 to 8 atoms and including the carbon atoms to which said $R^2$ or $R^3$ groups are bonded, said ring optionally containing one additional nitrogen and/or oxygen atom; and
Q represents a group of formula

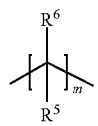

(i)

wherein m is 1 or 2, and
$R^5$ and $R^6$ represent, simultaneously or independently, a hydrogen atom, a $C_{1-6}$ linear, branched or cyclic alkyl or, a $C_{6-10}$ aromatic group optionally substituted; two distinct $R^6$ and/or $R^5$ groups, taken together, may form a $C_{3-8}$ saturated ring optionally substituted, including the atoms to which said $R^6$ and/or $R^5$, groups are bonded, and optionally containing one or two additional nitrogen or oxygen atoms;
the optional substituents of $R^1$, $R^2$, $R^3$, $R^5$, $R^6$ being one, two, three or four groups selected amongst i) halogens (in particular when said substituents are on aromatic moieties) iii) $C_{1-6}$ alkoxy, alkyl, alkenyl, or iv) a benzyl group or a fused or non-fused phenyl group, said group being optionally substituted by one, two or three halogen, $C_{1-8}$ alkyl, alkoxy, amino, nitro, ester, sulfonate or halo- or perhalo-hydrocarbon groups;
PP represents a $C_6$-$C_{50}$ bidentate ligand of formula

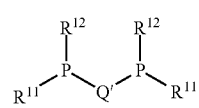

(C)

wherein $R^{11}$ and $R^{12}$, when taken separately, represent, simultaneously or independently, a $C_{3-6}$ branched or cyclic alkyl group or a $C_{6-10}$ aromatic group optionally substituted; and
Q' represents
a group of formula

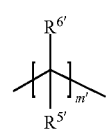

(i')

wherein m' is 1, 2, 3 or 4 and
$R^{5'}$ and $R^{6'}$ represent, simultaneously or independently, a hydrogen atom, a $C_{1-6}$ linear or branched alkyl group or a $C_{6-10}$ aromatic group optionally substituted; two distinct $R^{6'}$ and/or $R^{5'}$ groups, taken together, may form a $C_3$ to $C_8$ saturated or unsaturated ring optionally substituted, including the atoms to which said $R^{6'}$ and/or $R^{5'}$ groups are bonded, and optionally containing one or two additional nitrogen or oxygen atoms; or
a $C_{10}$-$C_{16}$ metallocenediyl, a 2,2'-diphenyl, a 1,1'-binaphthalene-2,2'-diyl, a benzenediyl, a naphthalenediyl, 2,3-bicyclo[2:2:1]hept-5-enediyl, 4,6-phenoxazinediyl, 4,5-(9,9-dimethyl)-xanthenediyl, or bis(phen-2-yl)ether group optionally substituted;
the optional substituents of $R^{5'}$, $R^{6'}$, $R^{11}$ and $R^{12}$ are one to five halogens (in particular when said substituents are on aromatic moieties), or one, two or three i) $C_{1-6}$ linear or branched alkyl alkoxy, groups or halo- or perhalo-hydrocarbon, amine groups, ii) COOR$^h$ wherein $R^h$ is a $C_{1-6}$ linear, branched or cyclic alkyl group, iii) NO$_2$ group, or iv) a benzyl group or a fused or non-fused phenyl group, said group being optionally substituted by one, two or three halogen, $C_{1-8}$ alkyl, alkoxy, amino, nitro, ester, sulfonate or halo- or perhalo-hydrocarbon groups; and each R represents, simultaneously or independently, a $C_2$-$C_{12}$ hydrocarbon group branched or cyclic in the $\alpha$ and/or $\beta$ position, and said hydrocarbon group is optionally comprising one to five heteroatom selected amongst halogen, oxygen and nitrogen atoms.

* * * * *

UNITED STATES PATENT AND TRADEMARK OFFICE
CERTIFICATE OF CORRECTION

PATENT NO.         : 9,090,534 B2
APPLICATION NO.    : 14/349811
DATED              : July 28, 2015
INVENTOR(S)        : Dupau et al.

It is certified that error appears in the above-identified patent and that said Letters Patent is hereby corrected as shown below:

Title Page:
Item (73) Assignee, delete "Firemenich SA" and insert -- Firmenich SA --.

In the Claims:
Column 56:
Lines 1-8, Claim 3, delete formula (B') and insert

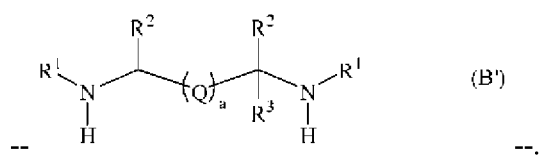

Signed and Sealed this
Twenty-fourth Day of November, 2015

Michelle K. Lee
*Director of the United States Patent and Trademark Office*